(12) United States Patent
Kent et al.

(10) Patent No.: US 8,618,049 B2
(45) Date of Patent: Dec. 31, 2013

(54) ESTER INSULIN

(76) Inventors: Stephen B. H. Kent, San francisco, CA (US); Youhei Soma, Tokyo (JP)

( * ) Notice: Subject to any disclaimer, the term of this patent is extended or adjusted under 35 U.S.C. 154(b) by 0 days.

(21) Appl. No.: 13/394,646

(22) PCT Filed: Sep. 7, 2010

(86) PCT No.: PCT/US2010/047961
§ 371 (c)(1),
(2), (4) Date: Mar. 7, 2012

(87) PCT Pub. No.: WO2011/031662
PCT Pub. Date: Mar. 17, 2011

(65) Prior Publication Data
US 2012/0220522 A1 Aug. 30, 2012

Related U.S. Application Data

(60) Provisional application No. 61/240,409, filed on Sep. 8, 2009.

(51) Int. Cl.
*A61K 38/28* (2006.01)
*A61P 3/04* (2006.01)
*A61P 3/10* (2006.01)
*A61P 3/08* (2006.01)
*C07K 14/62* (2006.01)

(52) U.S. Cl.
USPC .......................................... 514/6.2; 530/303

(58) Field of Classification Search
None
See application file for complete search history.

(56) References Cited

U.S. PATENT DOCUMENTS

| | | | |
|---|---|---|---|
| 3,847,893 A | 11/1974 | Brandenburg et al. |
| 3,883,496 A | 5/1975 | Geiger |
| 3,883,500 A | 5/1975 | Geiger et al. |
| 3,907,763 A | 9/1975 | Brandenburg et al. |
| 3,996,268 A | 12/1976 | Carpenter et al. |
| 4,014,861 A | 3/1977 | Obermeier et al. |
| 4,343,898 A | 8/1982 | Markussen |
| 4,430,266 A | 2/1984 | Frank |
| 5,247,068 A | 9/1993 | Donachy et al. |
| 6,281,331 B1 | 8/2001 | Kang et al. |
| 6,852,694 B2 | 2/2005 | Van Antwerp et al. |

(Continued)

OTHER PUBLICATIONS

Sheh L et al "Design, synthesis, and testing of potential antisickling agents" Int J Peptide Protein Res 29:509-520. Published Apr. 1, 1987.*

(Continued)

*Primary Examiner* — Cecilia J Tsang
*Assistant Examiner* — Zachary J Miknis
(74) *Attorney, Agent, or Firm* — James A. Bradburne

(57) ABSTRACT

Compositions and methods related to ester insulin or derivatives thereof are provided. The compositions include $Glu^{44}$-$Thr^{B30}$ ester insulin, in which side chains of $Glu^{44}$ and $Thr^{B30}$ of native human insulin or an insulin analogue such as insulin lispro are covalently linked via a single ester bond. The ester insulin is efficiently folded, forming the desired disulfides. The $Thr^{B30}$-$Glu^{44}$ ester bond can be cleaved in vitro or in vivo to give the desired folded insulin with full biological activity. The ester insulin is readily prepared by total chemical synthesis, and amendable to cost-effective, large scale manufacturing. Also provided are pharmaceutical compositions and kits for use in practicing the subject methods. Also provided are methods of using the subject compositions and kits in the treatment of a variety of different disease conditions, particularly glucose metabolic disorders such as diabetes and obesity.

10 Claims, 5 Drawing Sheets

(56) References Cited

U.S. PATENT DOCUMENTS

| | | |
|---|---|---|
| 7,118,737 B2 | 10/2006 | Kochendoerfer et al. |
| 7,396,903 B2 | 7/2008 | Bogsnes et al. |
| 2002/0132760 A1 | 9/2002 | Van Antwerp et al. |

OTHER PUBLICATIONS

Choi and Kim "Controlled Release of Insulin from Injectable Biodegradable Triblock Copolymer Depot in ZDF Rats" Pharm Res 20:2008-2009. Published Dec. 2003.*

Sohma et al Design and Folding of [GluA4(ObThrB30)]Insulin ("Ester Insulin"): A Minimal Proinsulin Surrogate that Can be Chemically Converted to Human Insulin. Angew Chem Intl Ed 49:5489-5493. Published online May 27, 2010.*

Akaji et al., "Total synthesis of human insulin by regioselective disulfide formation using the silyl chloride-sulfoxide method," 1993, J. Am. Chem. Soc. 115:11384-11392.

Brandenburg et al., "The effect of a non-peptide interchain cross-link on the reoxidation of reduced insulin," Hoppe-Seyler's Z. Physiol. Chem., 1973, 354:613-627.

Brandenburg et al., "NalphaA1-N-epsilon B-29-crosslinked diaminosuberoylinsulin, a potential intermediate for the chemical synthesis of insulin," Hoppe-Seyler's Z. Physiol. Chem., 1973, 354:1521-1524.

Busse et al., "Synthesis and properties of carbonylbis(methionyl)insulin, a proinsulin analogue which is convertible to insulin by cyanogen bromide cleavage," Biochemistry,1976,15(8):1649-1657.

Ciszak et al. "Role of C-terminal B-chain residues in insulin assembly: the structure of hexameric LysB28ProB29—human insulin," Structure, 1995, 3(6):615-622.

Dawson et al., "Synthesis of proteins by native chemical ligation," Science, 1994, 266:776-779.

Geiger et al., "Insulin synthesis from natural chains by means of reversible bridging compounds," Biochem. Biophys. Res. Commun., 1973, 55:60-66.

Hua et al., "Mechanism of Insulin Chain Combination Asymmetric Roles of A-Chain α-Helices in Disulfide Pairing," J. Biol. Chem., 2002, 277:43443-43453.

Johnson et al., "Insights into the mechanism and catalysis of the native chemical ligation reaction," J. Am. Chem. Soc., 2006, 128:6640-6646.

Johnson et al., "Towards the total chemical synthesis of integral membrane proteins: a general method for the synthesis of hydrophobic peptide-athioester building blocks," Tetrahedron Lett., 2007, 48:1795-1799.

Katsoyannis et al., "Insulin peptides. X. The synthesis of the B-chain of insulin and its combination with natural or synthesis A-chain to generate insulin activity," J. Am. Chem. Soc., 1964, 86(5):930-932.

Kemmler et al., "Studies on the conversion of proinsulin to insulin I. Conversion in vitro with trypsin and carboxypeptidase B," J. Biol. Chem., 1971, 246: 6786-6791.

Marglin et al., "The synthesis of bovine insulin by the solid phase method," J. Am. Chem. Soc., 1966, 88 (21):5051-5052.

Mayer et al., "Insulin structure and function," Biopolymers (Peptide Science), 2007, 88:687-713.

Nakagawa et al., "Chiral mutagenesis of insulin. Contribution of the B20-B23 beta-turn to activity and stability," J. Biol. Chem., 2006, 281:22386-22396.

Obermeier et al., "A new bifunctional reagent for the intramolecular crosslinking of insulin," Hoppe-Seyler's Z. Physiol. Chem., 1975, 356:1631-1634.

Oyer et al., "Studies on human proinsulin," J. Biol. Chem., 1971, 246:1375-1386.

Schnolzer et al. "In situ neutralization in Boc-chemistry solid phase peptide synthesis," Int. J. Peptide Protein Res., 1992, 40:180-193.

Sieber et al., "Total synthese von Human insulin. IV. Beschreibung der Endstufen," 1977, Helv. Chim. Acta 60:27-37.

Sohma et al., "Comparative properties of insulin-like growth factor 1 (IGF-1) and [Gly7D-Ala]IGF-1 prepared by total chemical synthesis," Angew. Chem. Int. Ed., 2008, 47:1102-1106.

Thim et al., "Secretion and processing of insulin precursors in yeast," Proc. Natl. Acad. Sci. USA, 1986, 83:6766-6770.

Tofteng et al., "Total synthesis of desB30 insulin analogues by biomimetic folding of single-chain precursors," ChemBioChem, 2008, 9:2989-2996.

Whittaker et al., "Characterization of the functional insulin binding epitopes of the full-length insulin receptor," J. Biol. Chem., 2005, 280(22):20932-20936.

Winter et al., "Renaturation of human proinsulin—a study on refolding and conversion to insulin," Anal. Biochem., 2002, 310:148-155.

* cited by examiner

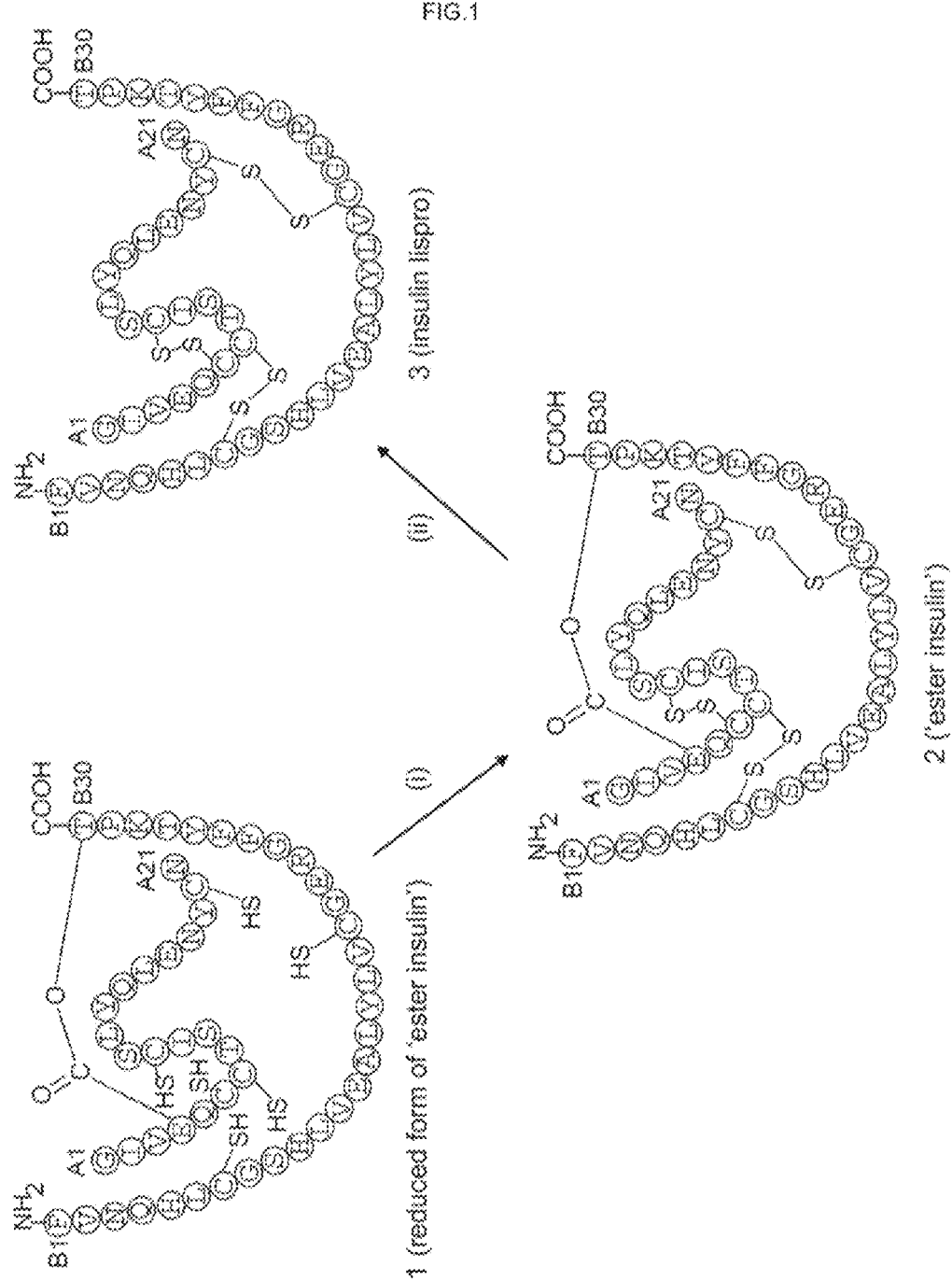

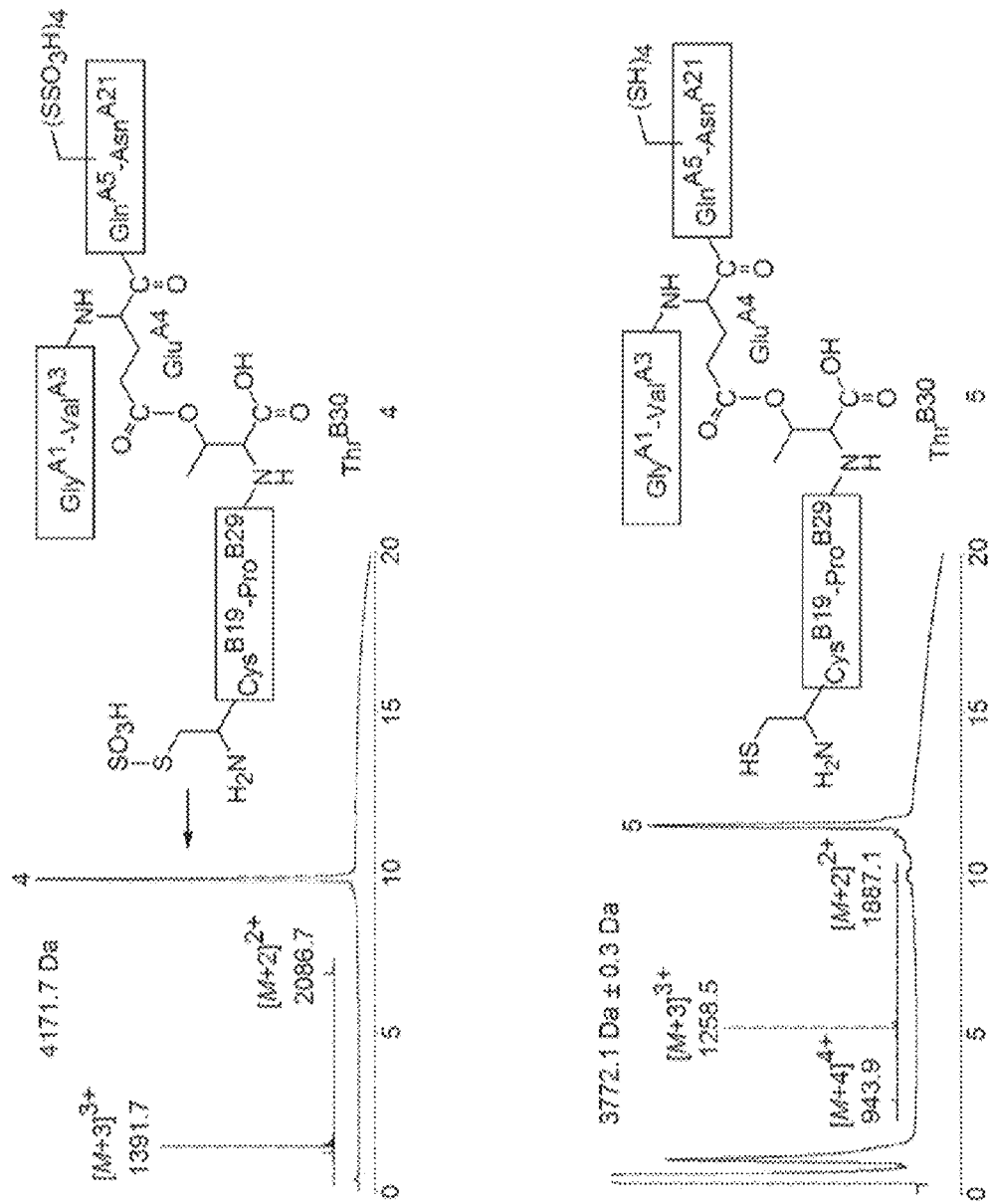

FIG. 3
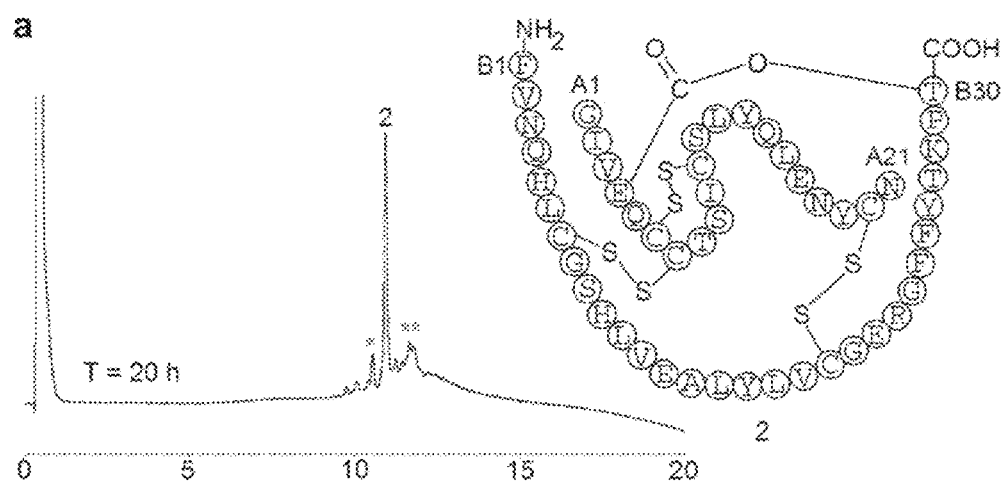
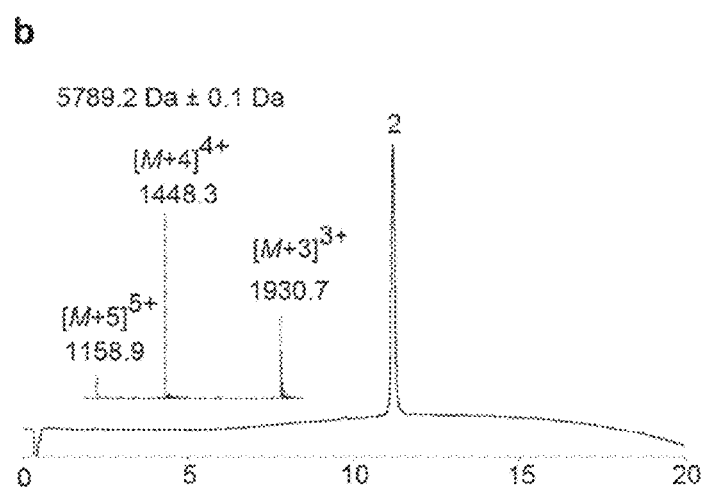

SEQUENCE LISTING

```
<160> NUMBER OF SEQ ID NOS: 3

<210> SEQ ID NO 1
<211> LENGTH: 21
<212> TYPE: PRT
<213> ORGANISM: Homo sapiens
<220> FEATURE:
<221> NAME/KEY: DISULFID
<222> LOCATION: (6)..(11)
<220> FEATURE:
<221> NAME/KEY: DISULFID
<222> LOCATION: (20)..(20)
<223> OTHER INFORMATION: Interchain disulfide

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens
<220> FEATURE:
<221> NAME/KEY: DISULFID
<222> LOCATION: (7)..(7)
<223> OTHER INFORMATION: Interchain disulfide
<220> FEATURE:
<221> NAME/KEY: DISULFID
<222> LOCATION: (19)..(19)
<223> OTHER INFORMATION: Interchain disulfide

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (7)..(7)
<223> OTHER INFORMATION: Interchain disulfide
<220> FEATURE:
```

```
-continued

<221> NAME/KEY: DISULFID
<222> LOCATION: (19)..(19)
<223> OTHER INFORMATION: Interchain disulfide

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30
```

ESTER INSULIN

CROSS-REFERENCE TO RELATED APPLICATION

This application claims priority benefit of U.S. provisional application Ser. No. 61/249,409, filed Sep. 8, 2009, which application is incorporated herein by reference in its entirety.

STATEMENT REGARDING FEDERALLY SPONSORED RESEARCH

This invention was made with government support under Grant No. 5RO1GM075993 awarded by the National Institute of Health. The government has certain rights in this invention.

FIELD OF THE INVENTION

The present invention relates to ester insulin and analogues/derivatives thereof, production and uses thereof.

BACKGROUND OF THE INVENTION

The native biosynthetic scheme of insulin involves an efficient folding/disulfides formation in a single chain precursor proinsulin molecule and subsequent enzymatic removal of the C-peptide to give mature insulin (Oyer et al., (1971) *J. Biol. Chem.* 246:1375-1386; and Kemmler et al., (1971) *J. Biol. Chem.* 246: 6786-6791). A proinsulin-based approach has been currently adopted in the recombinant production of insulin (Frank et al., *MMW Munch. Med. Wochenschr* (1983) 125(Suppl 1):14-20; and Thim et al. (1986) *Proc. Natl. Acad. Sci. USA* 83:6766-6770).

In current recombinant synthesis of human insulin (and analogs) as drug manufactures, the chemical diversification is limited to natural amino acids (Mayer et al., (2007) *Biopolymers (Peptide Science)* 88:687-713): Conversely, total chemical synthesis of human insulin permits the incorporation essentially any non-natural structure into the molecule, an apparent advantage that allows for full exploration of the medicinal chemistry of this important therapeutic molecule. However, an efficient chemical synthesis approach to human insulin is lacking (Mayer et al., (2007) supra). This apparent deficiency hampers not only the cost-effective chemical manufacture of insulin, but also the development of next generation insulin analogs containing non-natural chemical structure.

The difficulty of chemical insulin synthesis is mainly attributed to a low yield recombination of A- and B-chains via interchain disulfides formation. In addition, the disulfides-forming reaction requires an excess amount of A-chain (Hua et al. (2002) *J. Biol. Chem.* 277:43443-43453). An initial set of total chemical syntheses of insulin involved the inefficiency in three disulfides formation from separated A- and B-chains which were prepared by segment condensation (Meienhofer at al. (1963) *Z. Naturforsch.* 18b:1120-1121; Katsoyannis et al., (1964) *J. Am. Chem. Soc.* 86:930-932; and Du et al., (1965) *Sci. Sin.* 14:229-236) or solid phase peptide synthesis (Marglin et al., (1966) *J. Am. Chem. Soc.* 88:5051-5052). An alternative methodology with chemically directed formation of the disulfide bonds (Sieber et al. (1977) *Helv. Chim. Acta* 60:27-37; and Akaji et al., (1993) *J. Am. Chem. Soc.* 115:11384-11392) is complicated and has not found widespread use.

An alternative is to use a chemical tether to mimic the effect of covalently linking the A- and B-chains as found in proinsulin. Most of the previously studied chemically tethered insulin precursors have involved covalent linking of the N-terminal of the insulin A chain to the side chain of LysB29, near the C-terminal of the insulin B-chain (Brandenburg, D. & Wollmer, A. (1973) *Hoppe-Seyler's Z. Physiol. Chem.* 354: 613-627; Brandenburg et al. (1973) *Hoppe-Seyler's Z. Physiol. Chem.* 354:1521-1524; Geiger, R. & Obermeier, R. (1973) *Biochem. Biophys. Res. Commun.* 55:60-66; Obermeier, R. & Obermeier, R. (1975) *Hoppe-Seyler's Z. Physiol. Chem.* 356:1631-1634; and Busse, W-D. & Carpenter, F. H. (1976) *Biochemistry* 15:1649-1657). With a view to an efficient total synthesis of human insulin and analogues, a variety of different length chemical tethers between these two functionalities have been explored with both non-cleavable (Brandenburg, D. & Wollmer; A. (1973) supra) and cleavable tethers (Brandenburg et al. (1973) supra; Geiger et al. (1973) supra; Obermeier et al. (1975) supra; and Busse, W-D. & Carpenter, F. H. (1976) supra). It was found that tethers as short as 8 carbon atoms were effective in promoting high yield folding/disulfide formation (Brandenburg, D. & Wollmer, A. (1973) supra).

Recently, there have been attempts to extend the chemical tether approach to a more effective total chemical synthesis of insulin (Tofteng et al. (2008) *Chem Bio Chem* 9:2989-2996; and Sohma, Y. & Kent, S. B. H., "*Biomimetic synthesis of lispro insulin via a chemically synthesized 'mini-proinsulin' prepared by oxime-forming ligation*" Submitted). For example, synthesis of human insulin via chemically synthesized 'mini-proinsulin' prepared by oxime-forming ligation has been reported, in which an introduced temporary 'chemical tether' that links the N-terminal of the A chain to the C-terminal of the B chain, permitted the folding/formation of disulfides with high efficiency (Sohma, Y. & Kent, S. B. H, Submitted, supra). However, this later approach involved a relatively long/complicated chemical tether which made the synthesis laborious. In addition, it was necessary to remove the chemical tether enzymatically in a later step. Thus, various chemical production strategies reported to date for insulin are still far from practical for the efficient generation of insulin chemical analogues.

Ideal features of an optimal chemically tethered mini-proinsulin would include: straightforward preparation by existing synthetic methods; efficient folding/disulfide formation; and, ready chemical conversion to mature insulin. The present invention addresses these and other needs.

BRIEF SUMMARY OF THE INVENTION

Compositions comprising ester insulin, derivatives of ester insulin, intermediates, and related components, as well as methods of their production and use are provided. Also provided are kits that include one or more compositions of the invention, and for practicing one or more methods of the invention.

The ester insulin comprises A-chain and B-chain peptides of an insulin active agent, where the A-chain and B-chain peptides comprise amino acids corresponding to human insulin A-chain glutamate 4 ($Glu^{A4}$) and B-chain threonine 30 ($Thr^{B30}$) covalently linked through their side chains by an ester bond. The insulin active agent is a mature native insulin or biologically active analogue/derivative thereof, such as native human insulin, insulin lispro, insulin aspart, insulin gluisine, insulin glargine, or insulin determir. The ester insulin may be provided in reduced form, folded disulfide form, or combinations thereof. Also provided are compositions comprising mature insulin derived from an ester insulin of the invention, for example, by cleavage of the ester linkage in vitro and/or in vivo to produce the desired insulin active agent.

A featured composition comprises an ester insulin consisting essentially of the A-chain and B-chain peptides of native mature human insulin or analogue/derivative thereof, where the A-chain and B-chain peptides comprise glutamic acid and threonine amino acids corresponding to human insulin A-chain glutamate 4 ($Glu^{A4}$) and B-chain threonine 30 ($Thr^{B30}$), respectively, and where the side chain γ-carboxyl group of the glutamic acid residue corresponding to $Glu^{A4}$ and the side chain β-hydroxyl group of the threonine residue corresponding to $Thr^{B30}$ are directly linked via an ester bond. Thus in certain embodiments, the ester insulin is ester insulin human, ester insulin lispro, ester insulin aspart, ester insulin gluisine, ester insulin glargine, or ester insulin determir.

The intermediates include amino acids, peptides, and protected and unprotected derivatives thereof, capable of being employed for the synthesis of ester insulin, as well as other peptides. Of particular interest is a composition comprising: (i) a first amino acid or peptide comprising a glutamic acid residue having a side chain γ-carboxyl group; and (ii) a second amino acid or peptide comprising a threonine residue having a side chain β-hydroxyl group; wherein the glutamic acid residue and the threonine residue are covalently linked through the side chains by an ester bond.

The methods of production involve (i) providing an ester insulin, the ester insulin comprising A-chain and B-chain peptides of an insulin active agent, where the A-chain and B-chain peptides comprise amino acids corresponding to human insulin A-chain glutamate 4 ($Glu^{A4}$) and B-chain threonine 30 ($Thr^{B30}$) covalently linked through their side chains by an ester bond; and (ii) cleaving the ester linkage under conditions that form the insulin active agent.

The methods of treatment involve administering an effective amount of ester insulin or derivative thereof to a host in need thereof, where the ester insulin may be administered as an ester insulin, a mature insulin derived from an ester insulin (i.e., the insulin active agent), or a combination thereof. The kits comprise one or more compositions of the disclosure, for example, that find use and/or benefit from the methods of the disclosure.

The compositions, methods and kits of the invention have many advantages. For example, the invention is exemplified by the total chemical synthesis of a fast-acting human insulin analogue "insulin lispro" (also known as Humalog®) by an approach that is readily amenable to cost-effective, large scale manufacturing, via a $Glu^{A4}$-$Thr^{B30}$ ester insulin intermediate, in which the side chain γ-carboxyl group of $Glu^{A4}$ and the side chain β-hydroxyl group of $Thr^{B30}$ of insulin lispro are directly linked via an ester bond ($Glu^{A4}$-$Thr^{B30}$ ester insulin form insulin lispro referred to herein as "ester insulin lispro"). The ester insulin lispro, which can be constructed by total chemical synthesis, is efficiently folded, forming the desired disulfides with essentially the same efficiency as proinsulin; i.e., the $Thr^{B30}$-$Glu^{A4}$ direct covalent linkage is essentially as effective in promoting correct folding as the 35 amino acid residue C-peptide in proinsulin. Finally, the $Thr^{B30}$-$Glu^{A4}$ ester bond is cleaved by saponification in near-quantitative yield to give the mature folded insulin lispro with full biological activity.

The subject $Glu^{A4}$ and $Thr^{B30}$ residues of the fast acting insulin lispro exemplified herein are present in natural insulin molecules, and in insulin analogs, such as the fast-acting insulin aspart and insulin glulisine, as well as long acting insulins including insulin glargine, or can be engineered into other insulin analogues such as insulin detemir. As such, the present disclosure applies equally well to all forms of insulin, human or animal, broadly including analogue and native insulins. In particular, the ester insulin can be used to produce insulin as a generic drug, based on existing insulin forms currently on the market, as well as novel analogues of insulins. Ester insulin may also be used as a subcutaneous depot, slow release insulin.

BRIEF DESCRIPTION OF THE FIGURES

FIG. 1 depicts ester insulin strategy for the total chemical synthesis of an exemplary human insulin analogue, insulin lispro: (i) folding and disulfide formation; (ii) ester hydrolysis.

FIG. 3 depicts folding/disulfide formation of ester insulin lispro folded (2). Panel A: Folding was monitored by LC after 6 h (UV profiles at 214 nm are shown). Similar data were obtained after 20 h. Folding conditions were 1: 0.3 mg mL$^{-1}$, Tris: 20 mM, Cys: 8 mM, cystine: 1 mM, GnHCl: 1.5 M, pH=7.3, *[$Phe^{B1}$-$Val^{B18}$]-Cys(S—S) (which was produced by NCL of remained [$Phe^{B1}$-$Val^{B18}$]COS—$C_6H_4CH_2CO_2H$ with added Cys followed by the oxidation to form a disulfide bond, **Cys adducts. Panel B: purified ester insulin lispro folded (2). (Inset) On-line ESI-MS spectra taken at the top of the main peak in each chromatogram. Chromatographic separations were performed as described in Figure legend 3.

DESCRIPTION OF THE SPECIFIC EMBODIMENTS

Figure 2B:
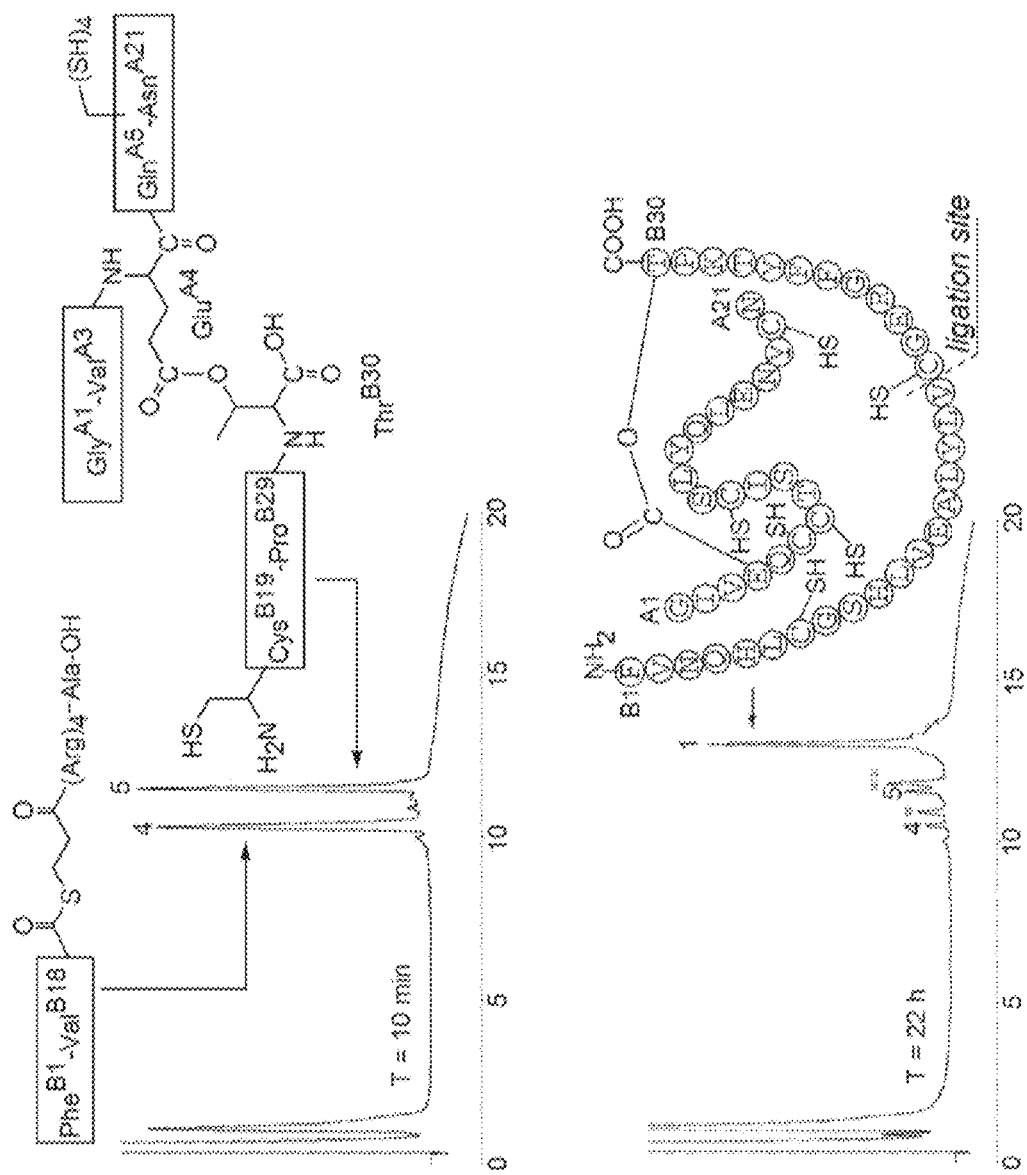
FIG. 2 depicts construction of ester insulin lispro reduced (1). Panel A: On-line ESI-MS spectra taken at the top of the main peak in each chromatogram. When $Cys^{B19}$-peptide(—$SSO_3H)_5$ (4) (upper panel A) was dissolved in 0.2 M $Na_2HPO_4$/6 M GnHCl in the presence of 200 mM MPAA and 30 mM TCEP, the five S-sulfo groups were rapidly reduced to free thiols in situ to give 5 (lower panel A). Following reduction, the mass decreased by 399.6 Da compared to that of S-sulfo form ($-SSO_3H)_5$, consistent with the formation of five thiol groups $(SH)_5$ to give 5. Panel B: Native chemical ligation (NCL) of $[Phe^{B1}-Val^{B18}]$-COαSR (6) with $Cys^{B19}$-peptide (5) to give the full-length polypeptide of ester insulin lispro (1). Reaction mixture at T=10 min (upper panel) and T=22 h (lower panel), *internal [Phe B1-ValB18]-CysB7-α-thiolactone, **[PheB1-$Val^{B18}$]-COS—$C_6H_4CH_2CO_2H$. The chromatographic separations were performed using a linear gradient (5-65%) of buffer B in buffer A over 15 min (buffer A=0.1% TFA in water; buffer B=0.08% TFA in acetonitrile) (UV profiles at 214 nm).

Compositions comprising ester insulin and derivatives thereof, intermediates, and related components, as well as methods of their production and use are provided. Also provided are kits that include one or more compositions of the invention, and for practicing one or more methods of the invention.

In one embodiment, a composition is provided comprising an ester insulin or derivative thereof, wherein the ester insulin comprises A-chain and B-chain peptides of an insulin active agent, the A-chain and B-chain peptides comprising amino acids corresponding to human insulin A-chain glutamate 4 (Glu$^{A4}$) and B-chain threonine 30 (Thr$^{B30}$) covalently linked through side chains by an ester bond. In one embodiment, the amino acids corresponding to human insulin A-chain Glu$^{A4}$ and B-chain Thr$^{B30}$ are glutamic acid and threonine, respectively, and the side chain γ-carboxyl group of the glutamic acid and the side chain β-hydroxyl group of the threonine are directly linked by the ester bond. In one embodiment, the insulin active agent is selected from the group consisting of human insulin, insulin lispro, insulin aspart, insulin gluisine, insulin glargine, and insulin determir. In one embodiment, the ester insulin is selected from the group consisting of ester insulin human, ester insulin lispro, ester insulin aspart, ester insulin gluisine, ester insulin glargine, and ester insulin determir. In one embodiment, the insulin active agent is capable of being produced by cleavage of the ester bond. In one embodiment, the insulin active agent or the ester insulin derivative is a product produced by cleavage of the ester bond. In one embodiment, the product produced by cleavage of the ester bond comprises a compound selected from the group consisting of human insulin, insulin lispro, insulin aspart, insulin gluisine, insulin glargine, and insulin determir. A featured embodiment is wherein the ester insulin is ester insulin lispro. Another featured embodiment is where the product produced by cleavage of the ester bond is insulin lispro. In one embodiment, the ester insulin or derivative thereof is the folded, disulfide form. In as many embodiments, the composition is comprised as a pharmaceutical formulation.

In one embodiment, a method of producing insulin is provided, the method comprising: (i) providing ester insulin, the ester insulin comprising A-chain and B-chain peptides of an insulin active agent, the A-chain and B-chain peptides comprising amino acids corresponding to human insulin A-chain glutamate 4 (Glu$^{A4}$) and B-chain threonine 30 (Thr$^{B30}$) covalently linked through side chains by a ester bond; and (ii) cleaving the ester bond under conditions that form the insulin active agent. In certain embodiments, the A-chain peptide comprises a glutamate residue corresponding to human insulin Glu$^{A4}$, and the B-chain peptide comprises a threonine residue corresponding to human insulin Thr$^{B30}$, the side chain γ-carboxyl group of the glutamate residue and the side chain β-hydroxyl group of the threonine residue being directly linked by the ester bond. In certain embodiments, the providing step (i) comprises: (a) chemically synthesizing the ester insulin; and (b) folding the ester insulin under conditions that form disulfide bonds corresponding to the insulin active agent. In a specific embodiment, cleaving is in vitro, such as wherein the cleaving in vitro is saponification.

In one embodiment, a method is provided that involves administering to a host in need thereof an effective amount of an ester insulin or derivative thereof, the method comprising administering to the host an effective amount of an ester insulin or derivative thereof effective to induce an insulin effect. A particular embodiment is where the insulin effect is a reduction of blood glucose level. One embodiment is where the host in need thereof is diabetic. A specific embodiment is wherein the ester insulin or derivative thereof is administered subcutaneously as a slow release depot.

In one embodiment, a composition is provided comprising a compound of the formula:

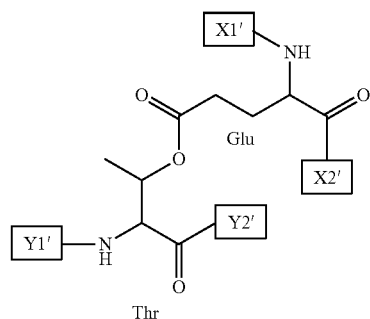

wherein: X1', X2', Y1', and Y2' are each individually selected from (i) a residue of an amino acid; (ii) a protecting group; (iii) a protected, partially protected, or unprotected amino acid; (iv) a protected, partially protected, or unprotected peptide; or (v) a linker, resin, surface or combination thereof. In one embodiment, X1' is selected from —H or protecting group; X2' is selected from —OH or protecting group; Y1' is selected from —H or protecting group; and Y2' is selected from —OH or protecting group. In another embodiment, X1' is a first protecting group that is present or absent; X2' is a second protecting group that is present or absent, and when present is orthogonal to the first protecting group; Y1' is a third protecting group that is present or absent, and when present is orthogonal to the first and second protecting groups; and Y2' is a forth protecting group that is present or absent, and when present is orthogonal to the first, second, and third protecting groups. In a specific embodiment, X1' is an Fmoc protecting group, X2' is an O-benzyl protecting group that is present or absent, Y1' is a Boc protecting group, and Y2' is an Oc-hexyl protecting group. In one embodiment, the X1'-Glu-X2' portion of the formula comprises insulin active agent A-chain. In one embodiment, the Y1'-Thr-Y2' portion of the formula comprises insulin active agent B-chain.

In as many embodiments, a subject ester insulin or derivative thereof composition of the disclosure is comprised as a subcutaneous slow release depot formulation.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described. The amino acid notations used herein are conventional, such as the following common amino acid abbreviations: Alanine, A, or Ala; Asparagine, N, or Asn; Aspartic acid, D, or Asp; Glutamine, Q, or Gln; Glutamic acid, E, or Glu; Histidine, H, or His; Isoleucine, I, or Ile; Leucine, L, or Leu; Lysine, K, or Lys; Phenylalanine, F, or Phe; Serine, S, or Ser; Threonine, T, or Thr; Tryptophan, W, or Trp; and Tyrosine, Y, or Tyr. Other amino acid and/or peptide abbreviations employed herein will be are apparent to one of ordinary skill in the art. Unless defined otherwise, the standard amino acid abbreviations above refer to the L-conformation.

In further describing the subject invention, the subject compositions and methods of production are described first in greater detail, followed by a review of the various uses, formulations and kits.

Compositions and Methods

As summarized above, compositions are provided that include ester insulin. The ester insulin is a polypeptide molecule comprising the A- and B-chain peptides of an insulin active agent. The insulin active agent is a native insulin or biologically active analogue/derivative thereof. The A-chain and B-chain peptides of ester insulin include amino acids corresponding to human insulin A-chain glutamate 4 ($Glu^{A4}$) and B-chain threonine 30 ($Thr^{B30}$). The side chains of the amino acids corresponding to the A-chain $Glu^{A4}$ and B-chain $Thr^{B30}$ are covalently linked by an ester bond, e.g., the side chain γ-carboxyl group of a glutamic acid residue corresponding to $Glu^{A4}$ and the side chain β-hydroxyl group of a threonine residue corresponding to $Thr^{B30}$ are directly linked via an ester bond.

By "amino acid corresponding to human insulin" is intended an amino acid residue present at an analogous position of native human insulin by sequence and/or three dimensional alignment. A representative formula of mature native human insulin is shown below (SEQ ID NO:1 and SEQ ID NO:2), with standard three letter amino acid code, standard A- and B-chain numbering, and with disulfide bonds of the mature form depicted by extended solid lines connecting cysteine (Cys) residues.

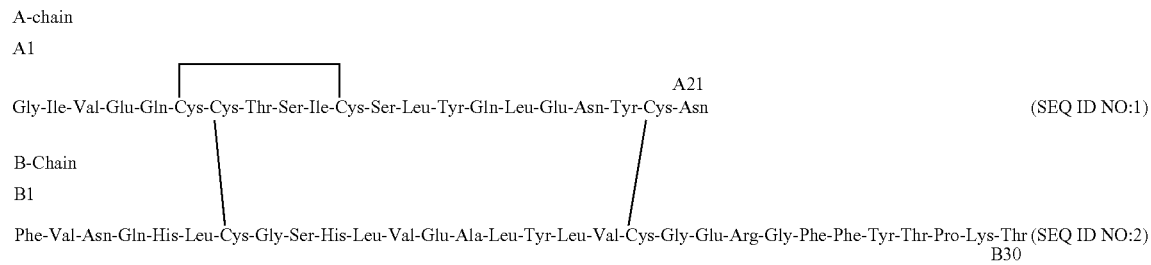

As is well known, mature native human insulin has 35 fewer amino acids than proinsulin, the later comprising intact B-C-A chain peptide. The C-peptide is abstracted from the center of the proinsulin sequence; the two other ends (the B chain and A chain) remain connected by disulfide bonds, as shown above.

Thus the glutamic acid at amino acid position 4 of the A-chain peptide ($Glu^{A4}$) of mature native human insulin, for example, corresponds to the glutamic acid at amino acid position 4 of the A-chain peptide ($Glu^{A4}$) of ester insulin lispro, or mature insulin lispro in which the ester bond is cleaved (e.g., see FIG. 1, which uses standard single letter amino acid code, with disulfides of mature insulin lispro depicted by extended solid lines with —S—S—; mature insulin lispro is also shown in below (SEQ ID NO:1 and SEQ ID NO:3), with standard three letter amino acid code, standard A- and B-chain numbering, and with disulfide bonds of the mature form depicted by extended solid lines connecting cysteine (Cys) residues).

A-chain
A1

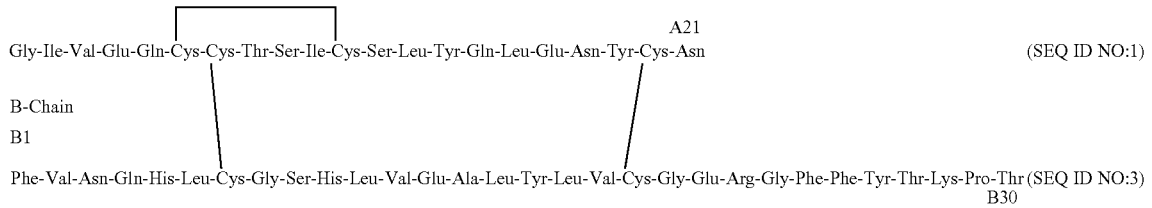

Gly-Ile-Val-Glu-Gln-Cys-Cys-Thr-Ser-Ile-Cys-Ser-Leu-Tyr-Gln-Leu-Glu-Asn-Tyr-Cys-Asn    A21    (SEQ ID NO:1)

B-Chain
B1

Phe-Val-Asn-Gln-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Lys-Pro-Thr (SEQ ID NO:3)
B30

As such, the corresponding amino acid(s) are easily identified by visual inspection of the relevant amino acid sequences, molecular modeling, or by using commercially available homology software programs, and the like.

Of specific interest is an ester insulin as described above, which comprises a structure according to formula I:

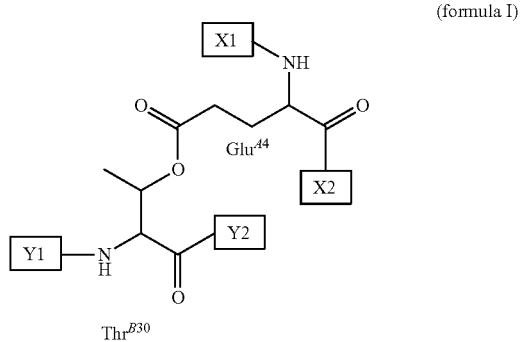

(formula I)

wherein: X1, X2, and Glu$^{A4}$ comprise the A-chain peptide of an insulin active agent, the Glu$^{A4}$ corresponding to Glu$^{A5}$ of human insulin; and Y1, Thr$^{B30}$, and Y2 comprise the B-chain peptide of the insulin active agent, the Thr$^{B30}$ corresponding to Thr$^{B30}$ of human insulin; or the pharmaceutically acceptable salts, solvates, hydrates, and prodrug forms thereof, and isomers thereof.

The term "amino acid" refers to the 20 genetically coded amino acids, rare or unusual amino acids that are found in nature, and any of the non-naturally occurring and modified amino acids; sometimes referred to as amino acid residues when in the context of a peptide, polypeptide or protein. By "peptide" is intended a polymer of at least two monomers, wherein the monomers are amino acids, sometimes referred to as amino acid residues, which are joined together via an amide; may have either a completely native amide backbone or an unnatural backbone or a mixture thereof; can be prepared by known synthetic methods, including solution synthesis, stepwise solid phase synthesis, segment condensation, and convergent condensation; can be synthesized ribosomally in cell or in a cell free system, or generated by proteolysis of larger polypeptide segments; can be synthesized by a combination of chemical and ribosomal methods, and may include backbone and/or side chain derivatives thereof, such as glycosylated, PEGylated and/or lipid modified versions.

Thus for example, in certain embodiments, X1 is Gly$^{A1}$-Val$^{A3}$ of native human insulin, X2 is Gln$^{A5}$-Asn$^{A21}$ of native human insulin, Y1 is Phe$^{B1}$-Lys$^{B29}$ of native human insulin or Phe$^{B1}$-Pro$^{B29}$ of insulin lispro, and Y2 is hydroxyl (—OH). In a specific embodiment, the ester insulin is ester insulin lispro, i.e., the Glu$^{A4}$-Thr$^{B30}$ ester of the fast-acting human insulin analogue "insulin lispro" (also known as Humalog®), in which the side chain γ-carboxyl group of Glu$^{A4}$ and the side chain β-hydroxyl group of Thr$^{B30}$ of insulin lispro are directly linked via an ester bond, or the pharmaceutically acceptable salts, solvates, hydrates, and prodrug forms thereof, and isomers thereof.

As such, amino acids corresponding to human insulin A-chain Glu$^{A4}$ and B-chain Thr$^{B30}$ are present in and correspond to analogous residues of natural insulin molecules including native human insulin, porcine insulin etc. and other insulin active agents, as well as insulin analogs, or can be engineered into other insulin analogues de novo. For example, human insulin analogues/insulin active agents of particular interest include, but are not limited to, the fast acting insulin lispro exemplified herein (penultimate lysine and proline residues on the C-terminal end of the B-chain of human insulin are reversed, i.e., Lys$^{B29}$→Pro$^{B29}$ and Pro$^{B28}$→Lys$^{B28}$ to yield human insulin analog Lys$^{B28}$+Pro$^{B29}$), the fast-acting insulin aspart (amino acid at position 28 of human insulin B-chain (B28), which is normally proline, is substituted with an aspartic acid residue, i.e., Pro$^{B28}$→Asp$^{B28}$) and insulin glulisine (double mutant Asn$^{B3}$→Lys$^{B3}$ and Lys$^{B29}$→Glu$^{B29}$, i.e., human insulin Lys$^{B3}$+Glu$^{B29}$), as well as long acting insulins including insulin glargine (substitution of glycine for asparagine at A21 and two arginines added to the carboxy terminal of B chain, i.e., Gly$^{A21}$+Arg$^{B31}$-Arg$^{B32}$) and insulin detemir (lysine amino acid at position B29 a fatty acid (myristic acid) is bound, i.e., Lys$^{B29\text{-}myristic\ acid}$). Additional examples of analogues include substitution or replacement of L-amino acids with D-amino acids, such as the insulin lispro Gly$^{B23L\text{-}Ala}$→Gly$^{B23D\text{-}Ala}$ mutant of insulin lispro designated "insulin lispro-[Gly$^{B23D\text{-}Ala}$]."

In certain embodiments, a threonine amino acid can be replaced or substituted by other suitable residues, such as a serine amino acid and the like. Similarly, a glutamic acid can be replaced or substituted by other suitable residues, such as with aspartic acid and the like. Thus, the ester insulin typically includes ester-forming residues capable of direct "linker-less" ester bond formation, which upon cleavage of the ester bond the side chains of the participating amino acids are regenerated. For example, ester-forming residues of this type include threonine-glutamic acid, threonine-aspartic acid, serine-glutamic acid, and serine-aspartic acid that are at a position in the ester insulin corresponding to Glu$^{A4}$ and Thr$^{B30}$ of human insulin. In a related embodiment, positioning of the ester bond can be adjusted by one or more substitutions, deletions and/or insertions to maximize folding of the ester insulin. In some embodiments, more than one ester bond can be employed. The desirability of such options can be readily assessed by molecular modeling and/or empirical methods, such as described below in the Experimental Methods; for example, distance and orientation of the side chains forming the ester bond are taken into consideration, and carries the proviso that the ester bond formed between ester-forming residues permits proper folding/disulfide formation. As noted above, however, glutamic acid-threonine ester forming residues at a position in the ester insulin corresponding to $Glu^{A4}$ and $Thr^{B30}$ of human insulin are of specific interest, as these residues and positions in the three dimensional insulin structure are sufficiently conserved in many insulins, including the commercially sold insulins.

The present disclosure therefore applies equally well to all forms of insulin, human or animal, broadly including analogue and native insulins. In particular, the ester insulin can be used to produce insulin as a generic drug, based on existing insulin forms currently on the market, as well as novel analogues of one or more additional insulins. Of specific interest is where the ester insulin consists essentially of the A-chain and B-chain amino acid sequences of native human insulin, or a human insulin analogue, such as an insulin analogue selected from the group consisting of insulin lispro, insulin aspart, insulin gluisine, insulin glargine, and insulin determir. Thus in certain embodiments, the ester insulin is selected from ester insulin human, ester insulin lispro, ester insulin aspart, ester insulin gluisine, ester insulin glargine, and ester insulin determir.

The ester insulin may be provided in reduced form, disulfide form, or combinations thereof. In the reduced form, the disulfide bonds are reduced, i.e., cysteine residues corresponding to human insulin $Cys^{B7}$, $Cys^{A7}$, $Cys^{B19}$, $Cys^{A20}$, $Cys^{A6}$, and $Cys^{A11}$ possess free thiol (—SH) side chains. In the disulfide form, the disulfides are formed, i.e., disulfide bonded cysteine residues corresponding to human insulin disulfide pairs $Cys^{B7}$-$Cys^{A7}$, $Cys^{B19}$-$Cys^{A20}$ and $Cys^{A6}$-$Cys^{A11}$, are formed. Combinations thereof include disulfide bonding intermediates.

Also provided are compositions that comprise mature insulin derived from an ester insulin of the disclosure, for example, by cleavage of the subject ester linkage in vitro and/or in vivo to produce the desired insulin active agent. Cleavage in vitro can be carried out by any suitable method, with saponification being of specific interest, such as in the Experimental Examples described below. In vivo cleavage can be by biodegradation in the body of a host by any suitable mechanism, such as by natural hydrolysis under physiological conditions, esterases present in the body, and/or physical/chemical means suitable for such purpose. Thus in certain embodiments, compositions are provided that include an ester insulin derivative formed by cleavage of the ester linkage of an ester insulin, the ester insulin derivative comprising a mature insulin (i.e., the insulin active agent) selected from the group consisting of native human insulin, or a human insulin analogue, such as an insulin analogue selected from the group consisting of insulin lispro, insulin aspart, insulin gluisine, insulin glargine, and insulin determir.

The intermediates include amino acids, peptides, and protected and unprotected derivatives thereof, capable of being employed for the chemical synthesis of ester insulin or any other ester-linked peptides of interest, such as described in the Experimental Examples below. Thus for example, compositions of specific interest are isolated and effectively pure compounds of formula II:

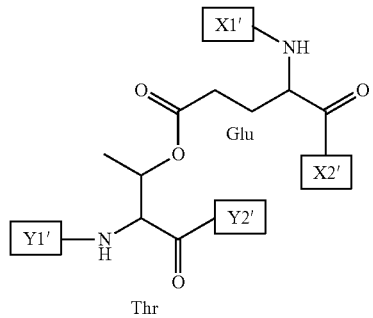 [SMILES: CNC(CCC(=O)OC(C)C(NC)C(C)=O)C(C)=O]

(formula II)

wherein: X1', X2', Y1', and Y2' are each individually selected from an organic or inorganic group. The organic or inorganic group is typically a group selected from (i) a residue of an amino acid, such as a radical selected from —S—, —SH, —O—, —OH, —NH—, or —NH$_2$; (ii) an amino acid protecting group, (iii) a protected, partially protected, or unprotected amino acid, (iv) a protected, partially protected, or unprotected peptide, or (v) a resin or surface.

Of particular interest are compounds of formula II comprising a first peptide having a glutamic acid residue flanked by X1' and X2' as depicted in formula II (i.e., X1'-Glu-X2'), and a second peptide having a threonine residue flanked by Y1' and Y2' as depicted in formula II (i.e., Y1'-Thr-Y2'), where the first and second peptides are covalently linked by an ester bond through the side chain γ-carboxyl group of the glutamic acid residue and the side chain β-hydroxyl group of the threonine residue as depicted in formula II.

In certain embodiments, compounds of formula II comprise an unprotected, partially protected, or fully unprotected dipeptide intermediate, wherein: X1' is selected from —H or protecting group; X2' is selected from —OH or protecting group; Y1' is selected from —H or protecting group; and Y2' is selected from —OH or protecting group. Of specific interest are compounds of formula II that comprise an orthogonally protected dipeptide intermediate, such as where: X1' is a first protecting group that is present or absent; X2' is a second protecting group that is present or absent, and when present is orthogonal to the first protecting group; Y1' is a third protecting group that is present or absent, and when present is orthogonal to the first and second protecting groups; and Y2' is a fourth protecting group that is present or absent, and when present is orthogonal to the first, second, and third protecting groups.

By "orthogonal protecting group" is intended a protecting group cleavable under conditions different from cleavage of a second protecting group. For example, compounds of formula II include compounds illustrated in the Experimental Examples described below, including orthogonally protected dipeptide intermediates, where X1' is an Fmoc protecting group, X2' is an O-benzyl protecting group that is present or absent, Y1' is a Boc protecting group, and Y2' is an O-cyclohexyl protecting group, where "Boc" refers to tert-butoxycarbonyl, and "Fmoc" refers to 9H-fluorenylmethoxycarbonyl, such as illustrated below.

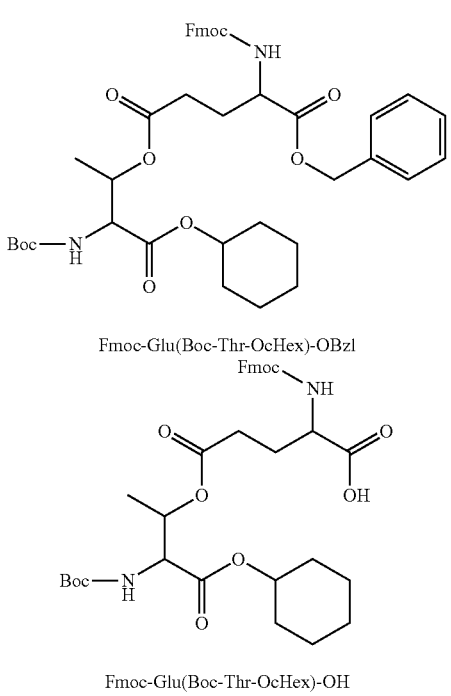

Fmoc-Glu(Boc-Thr-OcHex)-OBzl

Fmoc-Glu(Boc-Thr-OcHex)-OH

The methods of production involve (i) providing an ester insulin, and (ii) cleaving the ester linkage under conditions that form a biologically active insulin. A featured method of production comprises (i) providing an insulin A-chain peptide comprising a glutamate residue corresponding to human insulin $Glu^{44}$ covalently linked to an insulin B-chain peptide comprising a threonine residue corresponding to human insulin $Thr^{B30}$, where the $Glu^{44}$ and the $Thr^{B30}$ are covalently linked though their side chains by an ester linkage, and (ii) cleaving the ester linkage under conditions that form a biologically active insulin.

In certain embodiments, the ester insulin is provided by (i) synthesizing ester insulin, and (ii) folding the ester insulin under conditions suitable for forming the desired disulfides of the ester insulin. In certain embodiments, the folding and formation of disulfides is with an efficiency comparable to proinsulin (i.e., the $Thr^{B30}$-$Glu^{44}$ direct covalent linkage is essentially as effective in promoting correct folding as the 35 amino acid residue C-peptide in proinsulin).

Ester insulin synthesis can be carried out by any suitable method, such as stepwise chain assembly, segment condensation, convergent synthesis, chemical ligation, or a combination thereof. For example, the peptides may be synthesized by solution and/or solid phase chemistry techniques known in the art, such as by Fmoc and/or Boc stepwise chain assembly. Peptides fragments may be synthesized and subsequently combined or linked together to form the desired peptide sequences in solution by chemical ligation, segment and/or convergent synthesis. For instance, of particular interest is peptide synthesis by segment condensation, such as described in U.S. Pat. No. 6,281,331 (incorporated herein by reference). Chemical ligation includes an aqueous compatible ligation chemistry such as native chemical ligation (Dawson, et al., Science (1994) 266:776 779; Kent, et al., WO 96/34878), extended general chemical ligation (Kent, et al., WO 98/28434), oxime-forming ligation (Rose, et al., J. Amer. Chem. Soc. (1994) 116:30 33), thioester forming ligation (Schnolzer, et al., Science (1992) 256:221 225), thioether forming ligation (Englebretsen, et al., Tet. Letts. (1995) 36(48):8871 8874), hydrazone forming ligation (Gaertner, et al., Bioconj. Chem. (1994) 5(4):333 338), and thiazolidine forming ligation and oxazolidine forming ligation (Zhang, et al., Proc. Natl. Acad. Sci. (1998) 95(16):9184 9189; Tam, et al., WO 95/00846) or by other methods (Yan, L. Z. and Dawson, P. E., "Synthesis of Peptides and Proteins without Cysteine Residues by Native Chemical Ligation Combined with Desulfurization," J. Am. Chem. Soc. 2001, 123, 526 533; Gieselnan et al., Org. Lett. 2001 3(9):1331 1334; Saxon, E. et al., "Traceless" Staudinger Ligation for the Chemoselective Synthesis of Amide Bonds. Org. Lett. 2000, 2, 2141 2143; and U.S. Pat. No. 7,118,737; herein incorporated by reference). Of particular interest is a method of production such as described below in the Experimental Examples that involve a combination of stepwise chain assembly from a synthesis core comprising ester-linked glutamic acid and threonine residues, and native chemical ligation.

Finally, cleaving of the ester linkage is under conditions that form an effective amount of biologically active insulin, which as also discussed above can be in vitro and/or in vivo. For example, the $Thr^{B30}$-$Glu^{44}$ ester bond is readily cleaved in vitro by saponification (i.e., the hydrolysis of an ester under basic conditions to form an alcohol and the salt of a carboxylic acid) in near-quantitative yield to give the mature folded insulin with full biological activity. When cleavage is carried out in vivo, ester insulin may be used as a subcutaneous depot, slow release insulin. Of course a combination of in vitro and in vivo cleavage may be employed for a given end use.

Formulations

Also provided are pharmaceutical compositions containing the ester insulin or derivative thereof, e.g., in the form of a pharmaceutically acceptable salt. Thus, the insulin active agent such as the ester insulin or derivative thereof is administered as a single pharmaceutical formulation that, in addition to including an effective amount of the insulin active agent, includes other suitable compounds and carriers, and also may be used in combination with other active agents. The present invention, therefore, also includes pharmaceutical compositions comprising pharmaceutically acceptable excipients. The pharmaceutically acceptable excipients include, for example, any suitable vehicles, adjuvants, carriers or diluents, and are readily available to the public. The pharmaceutical compositions of the present invention may further contain other active agents as are well known in the art.

By way of illustration, the ester insulin or derivative thereof can be admixed with conventional pharmaceutically acceptable carriers and excipients (i.e., vehicles) and used in the form of dehydrated powders, aqueous solutions, tablets, capsules, elixirs, suspensions, syrups, wafers, and the like. Such pharmaceutical compositions contain, in certain embodiments, from about 0.1 to about 99% by weight of the active compound, and more generally from about 1 to about 30% by weight of the active compound. The ester insulin and derivatives thereof may be formulated in a suitable for a given end use.

One skilled in the art will appreciate that a variety of suitable methods of administering a formulation of the present invention to a subject or host, e.g., patient, in need thereof, are available, and, although more than one route can be used to administer a particular formulation, a particular route can provide a more immediate and more effective reaction than another route. Pharmaceutically acceptable excipients are also well-known to those who are skilled in the art, and are readily available. The choice of excipient will be determined in part by the particular compound, as well as by the particular method used to administer the composition.

Accordingly, there is a wide variety of suitable formulations of the pharmaceutical composition of the present invention. The following methods and excipients are merely exemplary and are in no way limiting.

A liquid composition will generally consist of a suspension or solution of the compound or pharmaceutically acceptable salt in a suitable liquid carrier(s), for example, aqueous or non-aqueous solvent, typically with one or more of a buffer, preservative, antioxidant, and tonicity modifier, such as a sugar, amino acid, surfactant, wetting agent, viscosity modifying agent, and the like, chelators or other suitable excipient. Alternatively, a liquid formulation can be prepared from a reconstitutable powder. For example, a powder containing active compound and suspending formulation can be reconstituted with an aqueous solution or non-aqueous solvent to form a solution, dispersion or suspension. Additionally, it may be desirable to add a coloring agent to make the dosage form more attractive in appearance or to help identify the product.

The compounds of the invention and their pharmaceutically acceptable salts that are active when given parenterally can be formulated for intramuscular, intrathecal, or intravenous administration. Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

A typical composition for intramuscular or intrathecal administration will be of a suspension or solution of active ingredient in an oil, for example, arachis oil or sesame oil. A typical composition for intravenous or intrathecal administration will be a sterile isotonic aqueous solution, e.g., as a solution in sterile water, normal saline or another pharmaceutically acceptable carrier. Examples of isotonic aqueous solutions include dextrose or sodium chloride, or a mixture of dextrose and sodium chloride. Other examples are lactated Ringer's injection, lactated Ringer's plus dextrose injection, NORMOSOL-M and dextrose, Isolyte E, acylated Ringer's injection, and the like. Optionally, a co-solvent, for example, polyethylene glycol, a chelating agent, for example, ethylenediamine tetracetic acid, and an anti-oxidant, for example, N-acetyl methionine, sodium metabisulphite and the like may be included in the formulation. Alternatively, the solution can be freeze dried and then reconstituted with a suitable solvent just prior to administration.

The compounds of the invention and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat. Suppository formulations are also provided by mixing with a variety of bases such as emulsifying bases or water-soluble bases.

Formulations suitable for topical administration may be presented as creams, gels, pastes, or foams, containing, in addition to the active ingredient, such carriers as are known in the art to be appropriate. In certain embodiments, the compounds of this invention and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches and other transdermal devices for the delivery of pharmaceutical agents is well known in the art. See, e.g., U.S. Pat. Nos. 5,681,580; 5,964,729; 7,404,815; and 7,314,859, herein incorporated by reference in its entirety. Such patches and transdermal devices may be constructed for continuous, pulsatile, or on demand delivery of pharmaceutical agents.

The subject formulations of the present invention can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

Unit dosage forms for administration may be provided wherein each dosage unit, for example, metered device dose, contains a predetermined amount of the composition. The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host. Those of skill in the art will readily appreciate that dose levels can vary as a function of the specific compound, the nature of the delivery vehicle, and the like. Suitable dosages and unit dosages for a given compound are readily determinable by those of skill in the art by a variety of means.

Subcutaneous formulations for fast-acting, intermediate-acting or long-acting ester insulins or derivatives thereof are of particular interest, including baseline formulations that more closely mimic or approximate normal basal insulin levels. Of particular interest are subcutaneous depot formulations that provide longer acting insulin. For example, subcutaneous formulations comprising ester insulin may result in longer acting insulin based on ester cleavage rate in vivo.

Thus, the various formulations described above employ well known approaches, and include insulin formulations known in the art for a variety of native and analogue insulins, such as those described in U.S. Pat. Nos. 7,575,761; 7,569,030; 7,521,069; 7,500,479; 7,490,603; 7,481,212; 7,476,652; 7,455,663; 7,452,860; 7,429,564; 7,393,544; 7,390,788; 7,387,996; 7,384,914; 7,314,859; 7,279,457; 7,255,102; 7,247,702; 7,241,586; 7,205,343; 7,205,277; 7,205,276; 7,192,919; 7,186,686; 7,141,542; 7,115,561; 7,112,561; 7,097,827; 7,087,215; 7,070,799; 7,052,678; 7,048,908; 7,028,686; 7,022,313; 7,021,309; 7,018,980; 6,960,561; 6,951,655; 6,921,527; 6,911,213; 6,906,027; 6,890,518; 6,869,930; 6,867,176; 6,852,694; 6,846,801; 6,838,076; 6,827,702; 6,797,258; 6,780,426; 6,756,053; 6,740,502; 6,737,401; 6,737,045; 6,734,162; 6,703,037; 6,688,304; 6,685,967; 6,680,091; 6,673,335; 6,655,379; 6,652,885; 6,647,987; 6,635,617; 6,624,141; 6,616,869; 6,589,560; 6,582,728; 6,582,393; 6,551,992; 6,531,448; 6,524,557;

6,517,860; 6,509,006; 6,495,120; 6,489,292; 6,485,706; 6,465,426; 6,465,006; 6,461,334; 6,451,286; 6,444,641; 6,444,226; 6,433,040; 6,432,383; 6,431,167; 6,431,166; 6,427,681; 6,408,854; 6,387,406; 6,375,975; 6,372,258; 6,368,272; 6,350,458; 6,350,432; 6,340,472; 6,335,316; 6,316,458; 6,315,984; 6,309,671; 6,306,420; 6,303,142; 6,290,987; 6,277,410; 6,268,335; 6,258,341; 6,250,298; 6,245,347; 6,235,224; 6,221,378; 6,211,144; 6,193,997; 6,191,105; 6,167,880; 6,153,211; 6,143,211; 6,142,972; 6,131,567; 6,098,615; 6,093,391; 6,085,753; 6,051,551; 6,024,090; 6,017,545; 6,004,583; 5,997,848; 5,981,594; 5,970,973; 5,965,160; 5,952,297; 5,945,187; 5,941,240; 5,915,378; 5,888,477; 5,884,620; 5,873,358; 5,858,398; 5,853,748; 5,837,276; 5,830,999; 5,830,853; 5,824,638; 5,743,250; 5,725,871; 5,707,641; 5,681,811; 5,672,581; 5,665;700; 5,660,846; 5,656,289; 5,653,987; 5,616,123; 5,582,591; 5,559,094; 5,547,929; 5,534,488; 5,531,925; 5,506,203; 5,438,040; 5,364,838; 5,359,030; 5,177,058; 5,120,710; 5,062,841; 4,963,526; 4,959,351; 4,910,021; 4,849,405; 4,849,227; 4,839,341; 4,701,440; and 4,652,548 (which references are herein incorporated by reference).

Applications

As summarized above, methods employing the compositions of the disclosure are provided, including methods of treatment, as well as research reagents and the like.

The methods of treatment involve administering an effective amount of ester insulin or derivative thereof to a host or subject in need thereof, e.g., for the treatment of a host suffering from disease or condition treatable by insulin. As such, the ester insulin may be administered as an ester insulin, a mature insulin derived from an ester insulin, or a combination thereof. A feature of the subject methods is that the ester insulin active agent is administered to the subject as the folded ester insulin (e.g., FIG. 1 compound 2) or as the folded mature insulin in which the ester linkage is cleaved (e.g., FIG. 1 compound 3). Slow release may be achieved by employing the folded ester insulin. Routes of administration may vary, but are typically those suitable for recombinant insulin (e.g., intravenous, subcutaneous, inhalation, and the like) as described above.

Ester insulin and analogues/derivatives thereof which may be present in the subject compositions for administration include, but are not limited to those compounds described above. As such, the scope of the present disclosure includes prodrugs of ester insulin. Such prodrugs are in general functional derivatives of the compounds that are readily convertible in vivo into the required compounds. Thus, in the methods of the present invention, the term "administering" encompasses administering the compound specifically disclosed or with a compound which may not be specifically disclosed, but which converts to the specified compound in vivo after administration to the subject in need thereof.

The subject methods find use in a variety of applications, wherein many applications the methods are modulating at least one cellular function associated with insulin function, such as glucose mediation. In this respect, the subject methods and composition find use in known applications of insulin, such as in treating diseases or disorders that are capable of being treated using insulin. Use of the subject compositions of the present invention is of particular utility in, for example, in the treatment of diseases and disorders including but not limited to glucose metabolic disorders, such as diabetes, obesity, and the like. In these capacities, use of the present inventive compositions will result in desired insulin activity.

As such, the subject methods and compositions find use in therapeutic applications in which insulin administration is indicated. A representative therapeutic application is the treatment of glucose metabolic disorders, e.g., diabetes, including type I and type II diabetes, particularly type I diabetes. By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

The dose administered to an animal, particularly a human, in the context of the present disclosure should be sufficient to effect a safe and prophylactic or therapeutic response in the animal over a reasonable time frame, i.e., an effective amount. One skilled in the art will recognize that dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound. Suitable doses and dosage regimens can be determined by comparisons to insulin agents that are known to achieve the desired outcome. Such dosages include dosages which result in a reduction in glucose levels, without significant side effects.

Particular applications in which the subject methods and compositions find use include those described for insulin, which are well known in the art.

Kits & Systems

Also provided are kits and systems that find use in practicing the subject methods, as described above. The kits may include one or more of the following: the reduced form, the non-reduced form, as well as intermediates, precursor components, and any biologically active form of ester insulin, including derivatives thereof. For example, kits and systems for practicing the subject methods may include one or more pharmaceutical formulations, which include ester insulin or ester insulin having its ester linkage cleaved, such as the human analog insulin lispro. As such, in certain embodiments the kits may include a single pharmaceutical composition, present as one or more unit dosages, where the composition includes the ester insulin. Of particular interest are kits that include an ester insulin or derivative thereof that include a delivery device in combination therewith (e.g., patches, syringes, insulin pens, inhalers, and the like). Monitoring devices, such as or glucose monitoring devices, strips, etc. may also be included.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The term "system" as employed herein refers to an ester insulin active agent composition and components thereof, present in a single or disparate composition, that are brought together for the purpose of practicing the subject methods. For example, separately obtained ester insulin active agent and a second composition brought together and coadministered to a subject, according to the present disclosure, are a system according to the present disclosure.

The following examples further illustrate the present invention and should not be construed as in any way limiting its scope.

EXPERIMENTAL

Abbreviations

MPAA, 4-mercaptophenylacetic acid (4-(carboxymethyl) thiophenol); NCL, native chemical ligation; TCEP, tris(2-carboxyethyl)phosphine hydrochloride; LC, liquid chromatography; RP-HPLC, reverse-phase HPLC; ESI-MS, electrospray ionization mass spectrometry; Boc, tert-butoxycarbonyl; Fmoc, 9H-fluorenylmethoxycarbonyl; TFA, trifluoroacetic acid.

Example 1

General Methods

Boc-amino acids were obtained from Peptide Institute, Inc. Fmoc-amino acids, 2-(1H-benzotriazole-1-yl)-1,1,3,3-tetramethyluronium hexafluorophosphate (HBTU) and 1-hydroxybenzotriazole (HOBt) were obtained from Peptides International, Inc. 1-Ethyl-3-(3-dimethyllaminopropyl)carbodiimide hydrochloride (EDC.HCl), N,N-dimethylaminopyridine (OMAP) and Fmoc-Glu-OBzl were from EMD Chemicals, Inc. 2-(1H-7-Azabenzotriazol-1-yl}-1,1,3,3-tetramethyluronium hexafluorophosphate (HATU) was from ChemPep, Inc. Trifluoroacetic acid (TFA) was from Halocarbon. All other chemical reagents were purchs8ed from Sigma-Aldrich or Fisher Scientific. Peptide compositions were evaluated by analytical reverse phase LC(-MS) using a gradient of 0.08% TFA in acetonitrile versus 0.1% TFA in water. For all the works reported in this paper, analytical HPLC was carried out as follows: C4 (2.1×50 mm) column using a linear gradient of 5-65% buffer a over 15 min at 40° C. with a flow rate of 0.5 mL min$^{-1}$ (buffer A=0.1% TFA in H$_2$O; buffer B=0.08% TFA in acetonitrile). The eluent was monitored at 214 nm, with on-line electrospray ionization mass spectrometry (ESI-MS) using an Agilent 1100 LC-ion trap. Peptides were purified on C4 or C8 silica with columns of dimension 10×250 mm. The silica used was TP Vydac. Crude peptides were loaded onto the prep column and eluted at a flow rate of 6 to 8 mL per minute with a shallow gradient (e.g. 5% B-55% B over 100 minutes) of increasing concentrations of solvent B (0.08% TFA in acetonitrile) in solvent A (0.1% TFA in water). Fractions containing the pure target peptide were identified by analytical LC, and were combined and lyophilized.

Example 2

Synthesis of Boc-Thr(Bzl)-OcHex

EDC.HCl (7.5 g, 40 mmol) was added to a stirring solution of Boc-Thr(Bzl)-OH (10 g, 32 mmol), cyclohexanol (5.0 mL, 48 mmol), and OMAP (0.66 g, 5.3 mmol) in OCM (75 mL) at 0° C. The mixture was warmed to room temperature (rt) over 30 min and stirred additionally overnight. After removal of the solvent in vacuo, the residue was dissolved in AcOEt, washed successively with 5% citric acid (3×), 5% NaHCO$_3$ (3×) and saturated NaCl (3×), dried over MgSO$_4$, and concentrated in vacuo. The resulting oil was purified by silica gel column chromatography (AcOE:hexane 1:8) to yield oily Boc-Thr(Bzl)-OcHex (12 g, 30 mmol, 95%). $^1$H NMR (CDCl$_3$ 400 MHz) 67.34-7.25 (m, 5H), 5.28 (d, J=9.6 Hz, 1H), 4.83-4.77 (m, 1H), 4.54 (d, J=11.6 Hz, 1H), 4.38 (d, J=11.6 Hz, 1H), 4.26 (dd, J=2.2, 9.6 Hz, 1H), 4.15 (dq, J=2.2, 6.4 Hz, 1H), 1.84-1.81 (m, 1H), 1.78-1.62 (m, 4H), 1.56-1.46 (m, 1H), 1.45 (s, 9H), 1.44-1.28 (m, 4H), 1.26 (d, J=6.4 Hz, 3H).

Example 3

Synthesis of Boc-Thr-OcHex

Pd/C (3.3 g) was added to a stirring solution of Boc-Thr (Bzl)-OcHex (11 g, 30 mmol) in AcOEt (80 mL), and the reaction mixture was vigorously stirred under a hydrogen atmosphere for overnight. The catalyst was filtered off through Celite and the solvent was removed in vacuo. The residue was purified by silica gel column chromatography, at first with AcOE:hexane 1:4 and then the desired product was washed out by AcOE:hexane 1:1 to give pure Boc-Thr-OcHex (8.6 g, 28 mmol, 94%). 1H NMR (CDCl$_3$ 400 MHz) b 5.26 (br. d, 1H), 4.89-4.82 (m, 1H), 4.30-4.20 (m, 2H), 1.94 (d, J=5.6 Hz, 1H), 1.86-1.83 (m, 2H), 1.74-1.70 (m, 2H), 1.57-1.48 (m, 3H), 1.46 (s, 9H), 1.44-1.30 (m, 3H), 1.25 (d, J=6.4 Hz, 3H).

Example 4

Synthesis of Fmoc-Glu(Boc-Thr-OcHex)-OBzl

EDC.HCl (5.1 g, 27 mmol) was added to a stirring solution of Boc-Thr-OcHex (6.6 g, 22 mmol), Fmoc-Glu-OBzl (10 g, 22 mmol), and DMAP (0.45 g, 3.6 mmol) in DCM (70 mL) at 0° C. The mixture was warmed to rt over 30 min. stirred additionally overnight, diluted with AcOEt, and washed successively with 5% citric acid (3×), 5% NaHCO$_3$ (3×) and saturated NaCl (3×). The organic layer was dried over MgSO$_4$ and the solvent was removed in vacuo. The residue was purified by silica gel column chromatography (AcOE:hexane 1:3) to yield Fmoc-Glu(Boc-Thr-OcHex)-OBzl (12 g, 16 mmol, 74%).

Example 5

Synthesis of Fmoc-Glu(Boc-Thr-OcHex)-OH

Pd/BaSO$_4$ (230 mg) was added to a stirring solution of Fmoc-Glu(Boc-Thr-OcHex)-OBzl (1.1 g, 1.4 mmol) in EtOH (20 mL), and the reaction mixture was vigorously stirred under a hydrogen atmosphere for 4 h. The catalyst was filtered off through Celite. The solvent was removed in vacuo and the crude product was filtered via silica gel at first with AcOE:

hexane 1:1 and then the final product was washed out by methanol to give pure Fmoc-Glu(Boc-Thr-OcHex)-OH (0.919, 1.3 mmol, 94%).

Example 6

CysB19-peptide(-SSO$_3$H)$_5$ Containing Thr$^{B30}$-Glu$^{44}$ Ester Moiety (4)

Side-chain protection for Boc-amino acids was as follows: Arg(Tos), Asn(Xan), Cys(4-CH$_3$Bzl), Glu(OcHex), Lys (2Cl—Z), Ser(Bzl), Thr(Bzl), Tyr(Br—Z). A protected Boc-Gln$^{45}$-Asn$^{A21}$-resin was prepared manually by "in situ neutralization" Boc chemistry stepwise solid phase peptide synthesis (Schnolzer et al. (1992) Int. J. Peptide Protein Res. 40:180-193) on —OCH$_2$—Pam-resin (at a 0.15 mmol scale). After the removal of N-terminal Boc group by treatment with neat TFA followed by neutralization with 10% N,N-diisopropylethylamine (DIEA) in DMF for 10 min, Fmoc-Glu(Boc-Thr-OcHex)-OH (215 mg, 0.33 mmol) was added to the resin after activation (30 sec) with 0.33 mmol DIC and 0.33 mmol HOBt in DCM-DMF (4:1), and coupled for 3 h. The Fmoc group of Glu$^{44}$ was removed by treatment with 20% piperidine in DMF (15 min). Fmoc-ValA3-OH, Fmoc-IleA2-OH and Fmoc-GlyA1-OH (3.0 mmol for each) were sequentially coupled in the presence of HATU (3.0 mmol) and DIEA (4.5 mmol) in DMF for 30 min (preactivation: 30 sec) after the removal of each preceding Fmoc group by 20% piperidine in DMF (15 min). Then, the Boc group (of Thr$^{B30}$) was removed by neat TFA and Boc-Pro$^{B29}$-OH (3.0 mmol) was coupled in the presence of HATU (3.0 mmol) and DIEA (5.4 mmol) in DMF for 30 min (pre-activation: 30 sec). The remaining peptide chain Boc-Cys$^{B19}$-Lys$^{B29}$ was assembled by in situ neutralization Boc chemistry stepwise solid phase peptide synthesis. The N-terminal Fmoc (of Gly$^{A1}$) and Boc (of Cys$^{B19}$) were successively removed by treatment with 20% piperidine and neat TFA, respectively. Peptides were deprotected and cleaved from the resin support by treatment with anhydrous HF containing p-cresol (90:10, v/v) for 1 h at 0° C. After evaporation of the HF under reduced pressure, crude peptide products were precipitated and triturated with chilled diethyl ether, and the peptide products were dissolved in 50% aqueous acetonitrile containing 0.1% TFA and lyophilized. Then, the resulting powder was dissolved in 6 M GnHCl/0.1 M Tris (pH 8.8, 12 mL) in the presence of Na$_2$SO$_3$ (3.7 mmol) and Na$_2$S$_4$O$_6$.2H2O (0.71 mmol), and stirred for 1 h. The crude products were purified by preparative HPLC, frozen at −78° C., and lyophilized. LC chart of purified peptide is depicted as FIG. 2A. LCMS gave: observed, 4171.7 Da; calculated (average isotopes), 4171.2 Da.

Example 7

[Phe$^{B1}$-Val$^{B18}$]-athioester-(Arg)$_4$-Ala-OH (6)

Peptide was prepared manually by "in situ neutralization" Boc chemistry stepwise solid phase peptide synthesis (Schnolzer et al. (1992) Int. J. Peptide Protein Res. 40:180-193) on HSCH$_2$CH$_2$CO-(Arg)$_4$-Ala-OCH$_2$-Pam-resin (α-thioester peptides) (Johnson et al. (2007) Tetrahedron Left. 48:1795-1799). Sidechain protection for amino acids was as follows: Arg(Tos), Asn(Xan), Cys(4-CH$_3$Bzl), Glu (OcHex), His(Bom), Ser(Bzl), Tyr(Br—Z). After completion of the chain assembly, peptides were deprotected and cleaved from the resin support by treatment with anhydrous HF containing p-cresol (90:10, v/v) for 1 h at 0° C. After evaporation of the HF under reduced pressure, crude peptide products were precipitated and triturated with chilled diethyl ether, and the peptide products were dissolved in 60% aqueous acetonitrile containing 0.1% TFA and lyophilized. LCMS gave: observed, 2826.5 Da; calculated, 2826.3 Da (with typical experimental uncertainty in LCMS mass measurement of 1 part in 10,000).

Example 8

Synthesis of Reduced Ester Insulin (1) by Native Chemical Ligation

Cys$^{B19}$-ester peptide(-SSO$_3$H)$_5$ (4) (12.5 mg, 3.0 µmol) was dissolved in aqueous solution containing 6 M GnHCl, 200 mM phosphate, 200 mM MPAA, 30 mM TCEP, pH 6.6, at concentration of 2 mM. After 10 min, the quantitative conversion to 5 was confirmed by LC-MS (observed, 3772.1±0.3 Da; calculated, 3771.2 Da). Then, [Phe$^{B1}$-Val$^{B18}$]-α-thioester-(Arg)$_4$-Ala-OH (6) (12.3 mg, 4.3 µmol) was added to the solution at concentration of 3 mM, and pH was adjusted to 6.9. After 22 h, the reaction mixture was diluted with ddH$_2$O (6×). The obtained suspension was centrifuged and the supernatant was removed. The resulting white precipitate was successively washed with 1 M GnHCl (3 mL, 3×) and ddH$_2$O (3 mL, 3×) to afford reduced polypeptide 1. The crude polypeptide was used for the subsequent folding reaction without further purification. LCMS gave: observed, 5795.0±0.1 Da; calculated, 5795.6 Da.

Example 9

Folding and Disulfide Formation

The crude polypeptide 1 was folded in 1.5 M GnHCl, 20 mM Tris, 8 mM cysteine, 1 mM cystine.HCl, pH 7.3, at a concentration of 0.3 mg mL$^{-1}$ with exclusion of air. During the folding reaction, no stirring was performed. After 6 h, HPLC analysis showed the folding was complete. The folding buffer was acidified with TFA (this caused the pH of the solution to drop to ~2) and the product purified by preparative HPLC to afford pure 2. Yield: 1.2 mg, 0.2 µmol, 7.3% (overall yield over two steps; NCL plus folding). The folded products were characterized by LC-MS; observed, 5789.2±0.5 Da; calculated, 5789.6 Da.

Example 10

Saponification

Ester insulin lispro folded 2 (0.3 mg, 0.051 µmol) was dissolved in 25% acetonitrile (in water) (2.4 mL) containing 25 mM sodium hydroxide, and the solution was shaken at 4° C. for 11 h. The reaction mixture was then acidified with TFA (this caused the pH of the solution to drop to ≈2) and purified by HPLC to afford pure 3. Yield: 0.28 mg, 0.048 µmol, 93%. The product was characterized by LC-MS (ESI); observed, 5807.8±0.2 Da; calculated, 5807.6 Da.

Example 11

Receptor-Binding Assays

Relative activity is defined as the ratio of analogue to wild-type human insulin required to displace 50 percent of specifically bound $^{125}$I-human Assays employed the B-isoform of insulin receptor (IR). Data were corrected for non-specific binding (amount of radioactivity remaining membrane associated in the presence of 1 mM human insulin). In all assays, the percentage of tracer bound in the absence of competing ligand was less than 15% to avoid ligand-depletion artifacts. Relative affinities of insulin analogs for the isolated IR (isoform B) were performed using a microliter plate antibody capture technique as described (Whittaker et al. (2005) *J. Biol. Chem.* 280:20932-20936). Microtiter strip plates (Nunc MI:Ixisorb) were incubated overnight at 4° C. with AU5 IgG (100 µl per well of 40 mg ml$^{-1}$ in phosphate-buffered saline). Binding data were analyzed by a two-site sequential model, with results discussed below.

Example 12

Design of Ester Insulin Lispro

In examining the three-dimensional structure of human lispro insulin (Ciszak et al. (1995) *Structure* 3:615-622), we noticed that the hydroxyl group on the beta carbon of Thr$^{B30}$ could be brought into contact with the side chain carboxyl group of Glu$^{A4}$. This indicated that a covalently linked ester intermediate might serve as a surrogate proinsulin, and thus promote efficient folding/disulfide formation in an insulin precursor molecule. As a key intermediate molecule for the total chemical synthesis of human insulin, a single-chain ester insulin was envisioned in which A- and B-chains of insulin are directly connected via a ester bond (i.e. with no additional auxiliary moiety as a tether) between β-hydroxyl group of Thr$^{B30}$ and γ-carboxyl group of Glu$^{A4}$ (See, e.g., FIG. 1).

Accordingly, a single-chain Thr$^{B30}$-Glu$^{A4}$ ester insulin was designed, in which A- and B-chain are connected via a direct ester bond (i.e. with no spacer moiety) between Thr$^{B30}$ and Glu$^{A4}$ side chains, for the total chemical synthesis of insulin lispro (FIG. 1). We envisioned an efficient folding/disulfides formation of the reduced form ester insulin lispro 1 to give 2 with Cys$^{B7}$-Cys$^{A7}$, Cys$^{B19}$-Cys$^{A20}$ and Cys$^{A6}$-Cys$^{A11}$, followed by saponification of the Thr$^{B30}$-Glu$^{A4}$ ester bond to give the mature insulin lispro molecule 3. For convenience, construction of the reduced form of ester insulin lispro (1) was designed to exploit native chemical ligation (NCL) (Dawson et al. (1994) *Science* 266:776-779) of [Phe$^{B1}$-Val$^{B18}$]-CO$^{\alpha}$SR (6) with Cys$^{B19}$-peptide containing Thr$^{B30}$-Glu$^{A4}$ ester moiety (5).

Example 13

Construction of Ester Insulin Lispro Polypeptide(-SH)$_6$

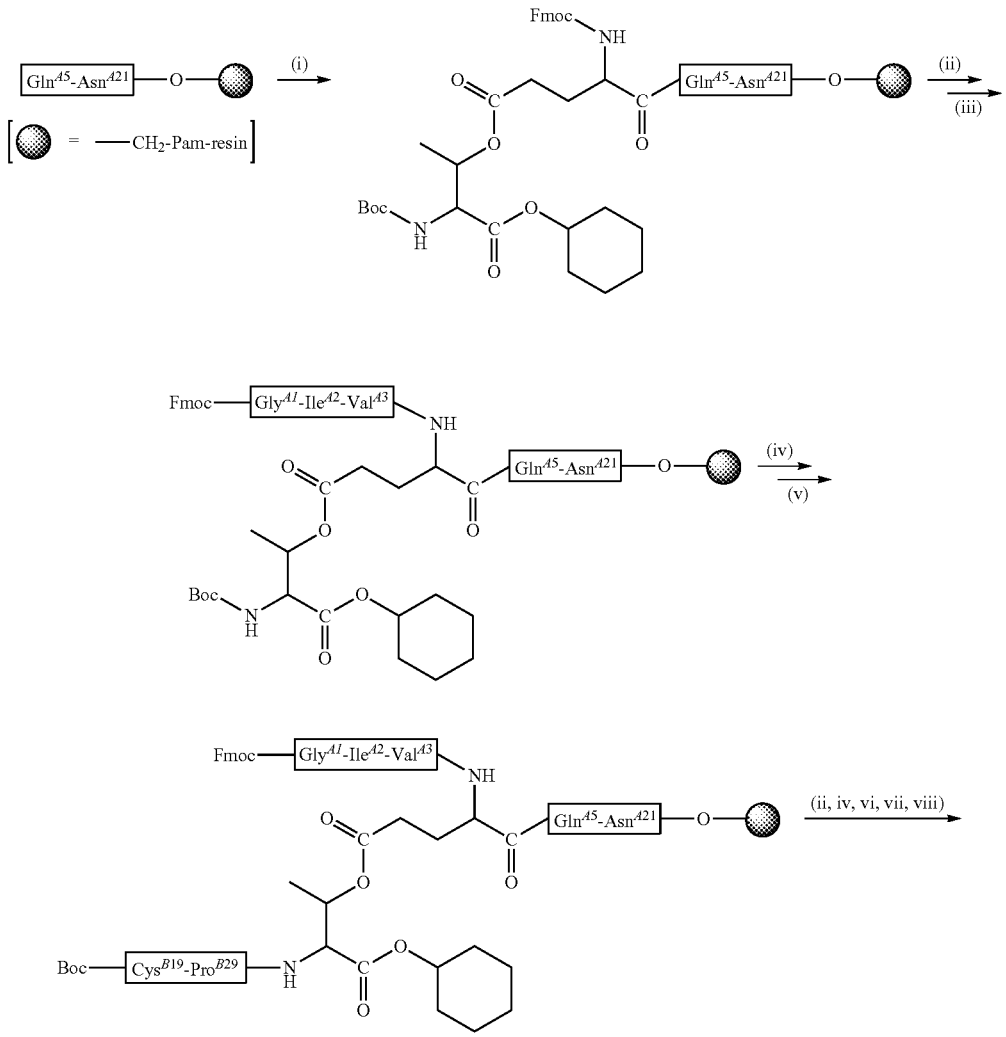

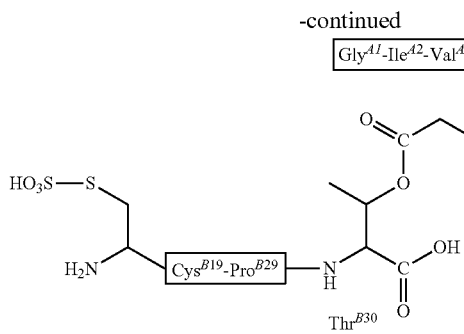
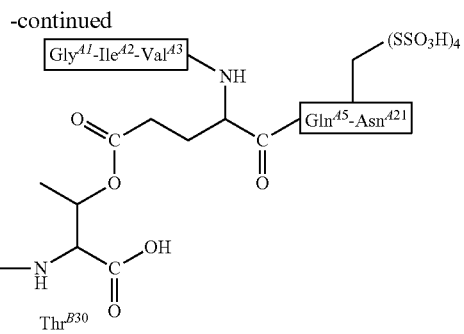

(i) Fmoc-Glu(Boc)-Thr-OHex)-OH, DIC (N,N'-diisopropylcarboiimide), HOBt (1-hydroxybenzotriazole), DCM-DMF (4:1); (ii) 20% piperdine in DMF; (iii)Fmoc—Xaa—OH, HATU, DIEA, DMF; (iv) TFA; (v) Boc-Pro$^{B29}$-OH, HATU, DIEA, DMF or Boc—Xaa—OH, HBTU, DIEA, DMF; (vi) HF, p-cresol; (vii) NaS$_4$O$_6$•2H$_2$O, 6M GnHCl/0.1M Tris (pH 8.8); (viii) preparative HPLC.

Scheme S2:

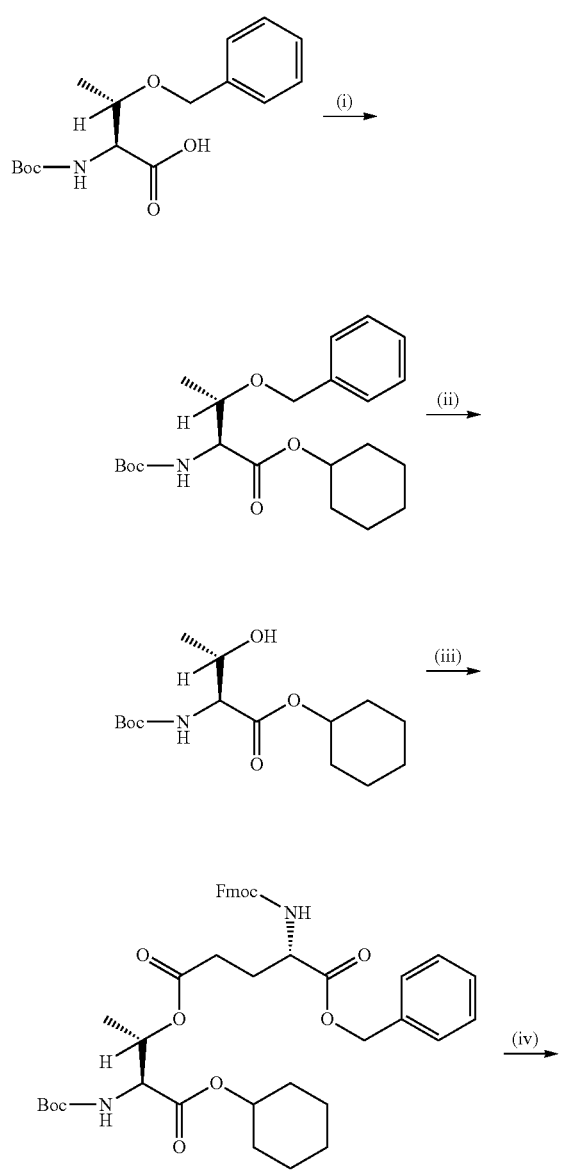

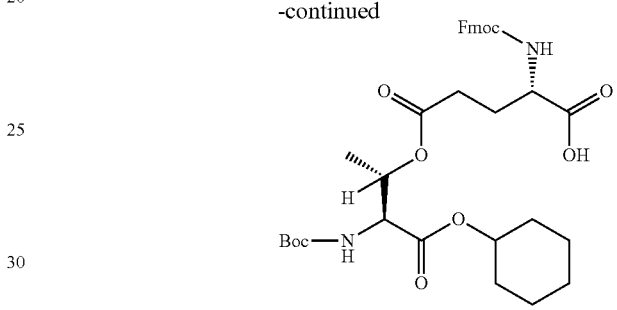

(i) cyclohexanol, EDC•HCl, DMAP, DCM, rt, overnight, 95%; (ii) Pd/C, H$_2$, AcOEt, rt, overnight, 94%; (iii) Fmoc-Glu-OBzl, EDC•HCl, DMAP, DCM, rt, overnight, 74%; (iv) Pd/BaSO$_4$, H$_2$, EtOH, rt, 4 h, 94%.

A Cys$^{B19}$-peptide (Thr$^{B30}$-Glu$^{A4}$ ester) as S-sulfo form at Cys$^{B19}$, Cys$^{A6}$, Cys$^{A7}$, Cys$^{A11}$ and Cys$^{A20}$ (4) was synthesized according to Scheme S1. Briefly, an ester dipeptide Fmoc-Glu(BocThr-OHex)-OH, which was prepared as depicted in Scheme S2 with an overall yield of 62%, was coupled to protected Gln$^{A5}$-Asn$^{A21}$-resin. The peptide Gly$^{A1}$-Val$^{A3}$ was constructed on N$^\alpha$-Gul$^{A4}$ by Fmoc-chemistry. Then, protected Cys$^{B19}$-Pro$^{B29}$ was constructed on N$^\alpha$-Thr$^{B30}$ by Boc-chemistry. The desired penta S-sulfonate compound 4 was obtained through the removal of Fmoc group of Gly$^{A1}$, removal of Boc group of Cys$^{B19}$, HF cleavage followed by sulfonation of five thiol groups.

When penta S-sulfonate 4 was dissolved in 0.2 M Na$_2$HPO$_4$/6 M GnHCl (2 mM) in the presence of 200 mM 4-mercaptophenylacetic acid (MPAA) (Johnson et al., (2006) *J. Am. Chem. Soc.* 128:6640-6646) and 30 mM tris(2-carboxyethyl)phosphine hydrochloride (TCEP), the five S-sulfonate groups of 4 were rapidly reduced to free thiols in situ to give 5 (FIG. 2A). Following reduction, the mass decreased by 399.6 Da compared to that of S-sulfonate form (SSO$_3$H)s, consistent with the formation of five thiol groups (—SH)$_5$ in 5. Then, [Phe$^{B1}$-Val$^{B18}$]-α-thioester-(Arg)$_4$-Ala-OH (6) was added (3 mM) and pH was adjusted to 6.9. According to previous findings in the synthesis of insulin-like growth factor 1 (IGF-1) (Sohma et al. (2008) *Angew. Chem. Int. Ed.* 47:1102-1106), we took advantage of an 'Arg-tag' in the C-terminal thioester leaving group of 6, which confers favorable handling properties for ligation by increasing the solubility of peptide (Johnson et al., (2007) *Tetrahedron Lett.* 48:1795-1799 (2007). The NCL was proceeded approximately 80% after 22 h (FIG. 2B). The efficient ligation to give full-length polypeptide of the ester insulin lispro 1 reaffirmed the significance of the improved aryl thiol catalyst MPAA for high yield ligation at a hindered Val-Cys site. In addition, side reactions derived from the Thr$^{B30}$-Glu$^{A4}$ ester moiety (such as hydrolysis of the ester) was not observed in the ligation reaction at the neutral pH. The reaction mixture was then diluted with ddH$_2$O (6×), and the obtained precipitate was successively washed with 1 M GnHCl and ddH$_2$O to provide full-length ester insulin lispro polypeptide 1.

Example 14

Folding and Disulfide Formation of Ester Insulin

Folding/disulfides formation of crude 1 was performed under the following conditions: about 0.3 mg mL$^{-1}$ 1, 20 mM Tris, 8 mM Cys, 1 mM cystine, 1.5 M GnHCl, pH=7.3. Folding of crude 1 was completed in 6 hours, with an estimated yield of 70% folded ester insulin lispro 2 as monitored by HPLC (FIG. 3A). Following oxidation, the mass decreased by 5.7±0.2. Da compared to that of reduced form, indicating the formation of three disulfide bonds in 2. A similar folding yield was obtained in oxidative folding conditions with 1 mM Cys and 8 mM cystine. This is in contrast to previous observations with His$_8$-Arg-proinsulin in which oxidative conditions gave higher folding yields (Winter et al. (2002) *Anal. Biochem.* 310:148-155). The excellent folding profile of 2 indicates that the Thr$^{B30}$-Glu$^{A4}$ ester linkage made the molecule favorable for the folding/disulfides formation just as well as C-peptide (35 amino acids long) does in the proinsulin molecule. The HPLC yield of 2 was also similar to those of oxime-linked 'mini-proinsulin' (Sohma, Y. & Kent, S. B. H., Biomimetic synthesis of lispro insulin via a chemically synthesized 'mini-proinsulin' prepared by oxime-forming ligation. Submitted) where the N-terminal of A-chain was connected to the C-terminal of B-chain. We isolated the folded ester insulin 2 after the purification (FIG. 3B). In the folding at pH=9.1, the proportion of 2 was apparently lower and bump peaks including Cys-adducts were increased (data not shown). A part of Thr$^{B30}$-Glu$^{A4}$ ester was also hydrolyzed at this pH. We isolated the folded ester insulin lispro 2, which was produced at pH=7.3, after the purification (FIG. 3B). Isolation yield of 2 over two steps (NCL+folding) was 7.3%.

Example 15

Production of Mature Insulin Lispro from Ester Insulin Lispro

Figure 4:
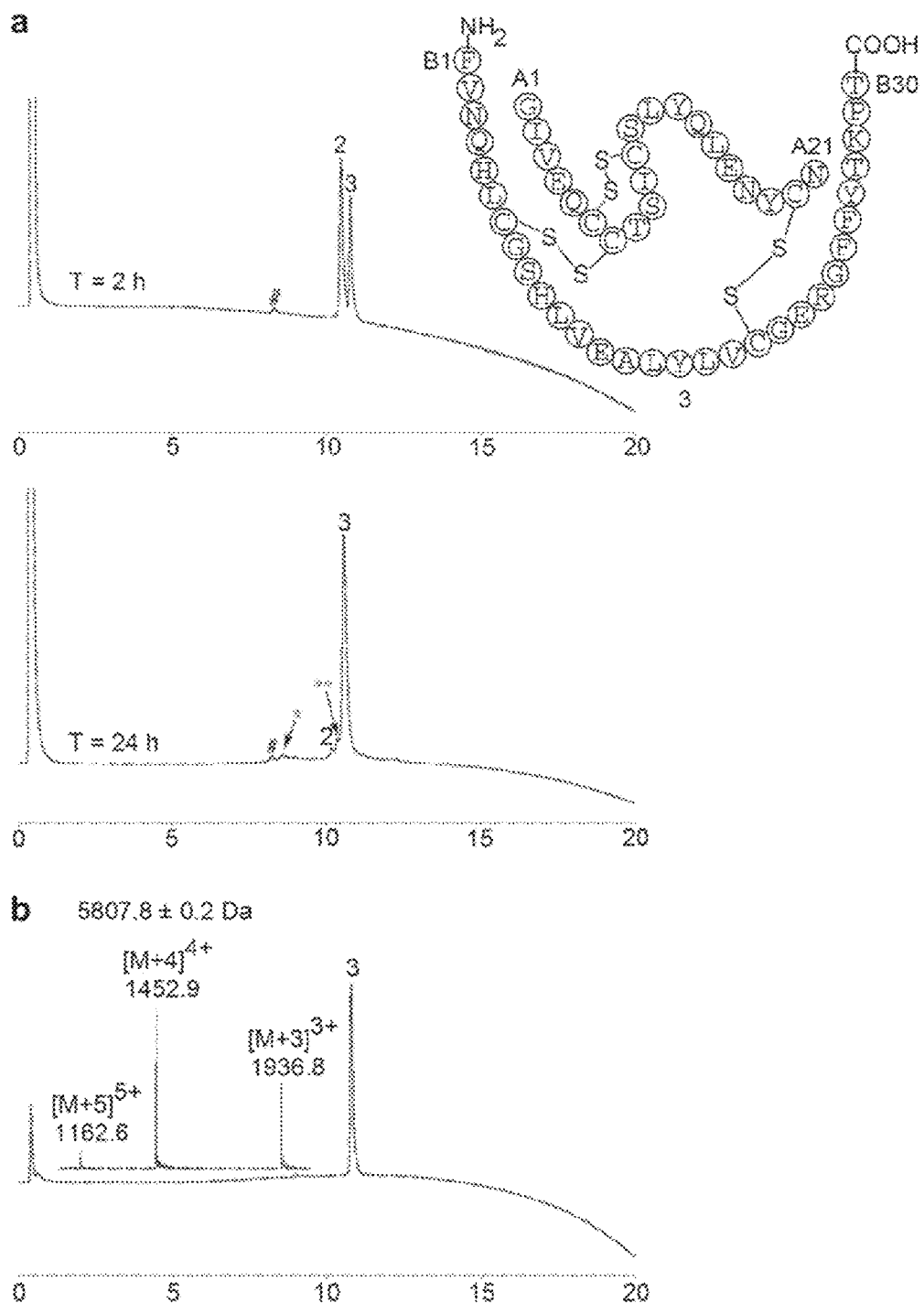
FIG. 4 depicts conversion of ester insulin lispro folded (2) to mature insulin lispro (3). Panel A: saponification of the ester insulin (2) to give mature insulin lispro (3). Conditions were (2): 0.05 mg mL$^{-1}$, NaOH: 0.1M, ACN—$H_2O$) (2.5: 7.5). Reaction mixture at T=2 hours (upper panel) and T=7 hours (lower panel), # non-peptidic compound. Panel B: purified insulin lispro (3). (Inset) On-line ESI-MS spectra taken at the top of the main peak in chromatogram. Chromatographic separations were performed as described in FIG. 2.

Saponification of the ester insulin lispro 2 with sodium hydroxide afforded mature insulin lispro 3 with the HPLC yield of ~90% (FIG. 4). Saponification of the ester insulin 2 was performed under the following conditions: about 0.12 mg mL$^{-1}$ 2, 25 mM sodium hydroxide, 25% acetonitrile (in water), 4° C. Under these conditions, the temperature of the saponification reaction was found to be critical for optimal production of mature insulin lispro. As shown in FIG. 4A, desired insulin molecule 3 was obtained with the HPLC yield of ~95% after 24 h reaction. A few percent of separated A- and B-chains were observed as side products probably due to disruption of disulfide bonds by sodium hydroxide. Following saponification, the mass increased by 18.5±0.2 Da compared to that of 2, consistent with the formation of 3. In the saponification reaction, a possible side reaction involving succinimide formation at the Asn$^{A21}$ was not observed. We obtained pure insulin lispro 3 after final purification (FIG. 4B). Isolation yield of 3 by the saponification of 2 was 93%.

The retention time on reverse phase LC of synthesized 3 was identical to that of an authentic sample of lispro insulin from our previous study (Sohma, Y. & Kent, S. B. H., Biomimetic synthesis of lispro insulin via a chemically synthesized 'mini-proinsulin' prepared by oxime-forming ligation. Submitted).

The ester insulin and the mature synthetic protein were also characterized by measurement of the relative binding affinity to the insulin receptor. Within experimental uncertainty, mature insulin lispro derived from ester insulin lispro was fully active, about the same as that of an authentic sample of lispro insulin. This further confirmed the formation of the correct disulfide bonds in the folded ester insulin lispro molecule. In contrast, ester insulin lispro was essentially inactive (less than 0.5%)

It is evident from the above results and discussion that the design and synthesis of [Glu$^{A4}$(O$^\beta$Thr$^{B30}$)]insulin lispro (1) precursor and (2) as a surrogate proinsulin with no additional auxiliary tether moiety can be employed in the total chemical synthesis of insulin and analogues/derivatives thereof. The ester insulin lispro compound, which was constructed using native chemical ligation, was efficiently folded with concomitant formation of disulfides under standard redox conditions. Thus the Thr$^{B30}$-Glu$^{A4}$ ester linkage made the precursor molecule essentially as favorable for folding as does the C-peptide in proinsulin. Finally, saponification of the ester insulin lispro gave the native folded insulin molecule in nearly quantitative yield. Synthetic lispro insulin produced by this route had full biological activity.

Example 16

Synthesis of Mature Insulin Lispro Analogue-[Gly$^{B23D-Ala}$] from Ester Insulin Lispro Analogue-[Gly$^{B23D-Ala}$]

To evaluate the utility of ester insulin for the efficient chemical synthesis of insulin analogues, we prepared the ester-containing polypeptide precursor of a Gly$^{B23L-Ala}$→Gly$^{B23D-Ala}$ mutant of insulin lispro designated "insulin lispro-[Gly$^{B23D-Ala}$]." The protein diastereomer insulin lispro-[Gly$^{B23D-Ala}$] was designed to investigate the contribution of the Gly$^{B23}$ residue to receptor recognition. As in ester insulin lispro, the polypeptide precursor of ester insulin lispro-[Gly$^{B23D-Ala}$] was efficiently folded with concomitant formation of three disulfide bonds, and the resulting oxidized ester insulin lispro-[Gly$^{B23D-Ala}$] was saponified in a similar manner and gave the desired insulin lispro-[Gly$^{B23D-Ala}$] (data not shown). The receptor binding affinity of the insulin lispro-[Gly$^{B23D-Ala}$] was (0.021±0.004) nm, a twofold higher activity than that of insulin lispro ((0.044±0.007) nm). The ester insulin lispro-[Gly$^{B23D-Ala}$] had 100-fold lower activity ((2.1±0.3) nm) compared with the insulin lispro-[Gly$^{B23D-Ala}$] mature form (data not shown). The twofold higher activity of the insulin lispro-[Gly$^{B23D-Ala}$] analogue suggests that the Gly$^{B23}$ residue of the insulin lispro contributes to receptor recognition by maintenance of the positive phi angle at B23, as was previously suggested by studies of insulin lispro (Nakagawa et al. (2006) *J. Biol. Chem.*, 281: 22386-22396).

To the best of our knowledge, this is the simplest approach for the total synthesis of human insulin by chemical means (Mayer et al. (2007) *Biopolymers (Peptide Science)* 88:687-713). We believe that the ester insulin lispro and other ester insulins will be a key molecule useful for the efficient generation of insulin and insulin analogues, and for use for the industrial scale production of insulin lispro and other insulins. As such, the subject invention represents a significant contribution to the art.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A composition comprising an ester insulin or derivative thereof, wherein the ester insulin comprises A-chain and B-chain peptides of an insulin active agent, the A-chain and B-chain peptides comprising amino acids corresponding in position to human insulin A-chain glutamate 4 ($Glu^{A4}$) and B-chain threonine 30 ($Thr^{B30}$), the amino acids covalently linked through their side chains by an ester bond.

2. The composition of claim 1, wherein the ester insulin is ester insulin lispro.

3. The composition of claim 1, wherein the insulin active agent is insulin lispro.

4. The composition of claim 1, wherein the ester insulin or derivative thereof is the folded, disulfide form.

5. The composition of claim 1, wherein the composition is comprised as a pharmaceutical formulation.

6. A method of producing insulin, the method comprising
   (i) providing ester insulin, the ester insulin comprising A-chain and B-chain peptides of an insulin active agent, the A-chain and B-chain peptides comprising amino acids corresponding in position to human insulin A-chain glutamate 4 ($Glu^{A4}$) and B-chain threonine 30 ($Thr^{B30}$), the amino acids covalently linked through their side chains by an ester bond; and
   (ii) cleaving the ester bond under conditions that form the insulin active agent.

7. A method of administering to a host in need thereof an effective amount of an ester insulin or derivative thereof, the method comprising administer to the host an effective amount of an ester insulin or derivative thereof effective to induce a reduction in blood glucose levels.

8. A composition comprising a compound of the formula:

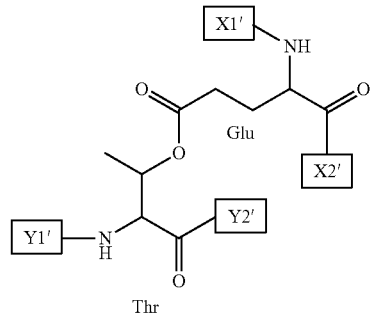

wherein: X1', X2', Y1', and Y2' are each individually selected from (i) a residue of an amino acid; (ii) a protecting group; (iii) a protected, partially protected, or unprotected amino acid; (iv) a protected, partially protected, or unprotected peptide; or (v) a linker, resin, surface or combination thereof; with the proviso that at least one of X1'-Glu-X2' or Y1'-Thr-Y2' comprises a peptide of an insulin active agent.

9. A kit comprising a composition according to claim 1 or claim 8 and a delivery device.

10. A composition according to claim 1 or claim 8, comprised as a subcutaneous slow release depot formulation.

* * * * *